(12) United States Patent
Maclean et al.

(10) Patent No.: US 11,959,486 B2
(45) Date of Patent: *Apr. 16, 2024

(54) STABLE LIQUID FORMULATION OF AMG 416 (ETELCALCETIDE)

(71) Applicant: AMGEN INC., Thousand Oaks, CA (US)

(72) Inventors: Derek Maclean, Los Altos, CA (US); Qun Yin, Palo Alto, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/400,044

(22) Filed: Aug. 11, 2021

(65) Prior Publication Data

US 2022/0042515 A1 Feb. 10, 2022

Related U.S. Application Data

(63) Continuation of application No. 16/430,322, filed on Jun. 3, 2019, now Pat. No. 11,162,500, which is a continuation of application No. 15/802,390, filed on Nov. 2, 2017, now Pat. No. 10,344,765, which is a continuation of application No. 14/908,481, filed as application No. PCT/US2014/044622 on Jun. 27, 2014, now Pat. No. 9,820,938.

(60) Provisional application No. 61/840,618, filed on Jun. 28, 2013.

(51) Int. Cl.
| | |
|---|---|
| *A61K 38/08* | (2019.01) |
| *A61K 9/00* | (2006.01) |
| *A61K 9/08* | (2006.01) |
| *A61K 47/12* | (2006.01) |
| *A61P 3/00* | (2006.01) |
| *A61P 3/14* | (2006.01) |
| *A61P 5/00* | (2006.01) |
| *A61P 5/18* | (2006.01) |
| *A61P 43/00* | (2006.01) |
| *F01D 15/10* | (2006.01) |
| *F04D 25/06* | (2006.01) |

(52) U.S. Cl.
CPC ........ *F04D 25/0606* (2013.01); *A61K 9/0019* (2013.01); *A61K 9/08* (2013.01); *A61K 38/08* (2013.01); *A61K 47/12* (2013.01); *F01D 15/10* (2013.01)

(58) Field of Classification Search
CPC .......... A61K 38/08; A61K 47/12; A61K 9/08; A61K 9/0019; A61P 5/00; A61P 5/18; A61P 3/00; A61P 3/14
See application file for complete search history.

(56) References Cited

U.S. PATENT DOCUMENTS

| | | |
|---|---|---|
| 6,846,911 B2 | 1/2005 | Kelly |
| 7,265,092 B2 | 9/2007 | Li |
| 8,067,532 B2 | 11/2011 | MacLean |
| 8,377,880 B2 | 2/2013 | Karim et al. |
| 8,987,200 B2 | 3/2015 | Bell et al. |
| 8,999,932 B2 | 4/2015 | Karim et al. |
| 9,278,995 B2 | 3/2016 | Karim et al. |
| 9,701,712 B2 | 7/2017 | Karim et al. |
| 9,820,938 B2 | 11/2017 | Maclean et al. |
| 10,344,765 B2 | 7/2019 | Maclean et al. |
| 2003/0119728 A1 | 6/2003 | Scheidl et al. |
| 2016/0220486 A1 | 8/2016 | Maclean et al. |

FOREIGN PATENT DOCUMENTS

| | | |
|---|---|---|
| CN | 102940879 A | 2/2013 |
| EP | 2264138 A1 | 12/2010 |
| EP | 2399604 A1 | 12/2011 |
| WO | WO 2004/105781 A2 | 12/2004 |
| WO | WO 2007/040711 A2 | 4/2007 |
| WO | WO 2008/067199 A3 | 6/2008 |
| WO | WO 2008/089491 A2 | 7/2008 |
| WO | WO 2011/014707 A2 | 2/2011 |
| WO | WO 2012/075375 A1 | 6/2012 |
| WO | WO 2012/170955 A1 | 12/2012 |
| WO | WO 2013/071262 A1 | 5/2013 |
| WO | WO 2014/210489 A1 | 12/2014 |
| WO | WO 2015/154031 A1 | 10/2015 |

OTHER PUBLICATIONS

Abelson and Fink, "Controlling for the Placebo Effect", Review of Ophthalmology, 2 pages, (2003).
Akers et al., "Peptides and Proteins as Parenteral Solutions", Pharmaceutical Development of Peptides and Proteins, Frokjaer et al. (eds.), Talor and Francis Limited pp. 144-155 (2000).
Allen et al., "Dosage Form Design: Pharmaceutical and Formulation Considerations", Ansel's Pharmaceutical Dosage Forms and Drug Delivery Systems, 9th Edition, Walters Kluwer, Lippencott Williams & Wilkins, Chapter 4, Section II, Drug Dosage Form and Drug Delivery System Design, pp. 90-142 (2012).
Bauer et al., "Pharmaceutical Technology", Georg Thieme Verlag, Rüdigerstraße 14, D-70469 Stuttgart 30, Chapter 9, *Parenterals, including blood preparations, serums, and vaccines*, pp. 225-228 (1993) German Language with English Translation.
"Buffer Solution", Wikipedia, 9 pages (2021) Online article downloaded from https://en.wikipedia.org/wiki/Buffer_solution.
ClinicalTrials.gov archive, "Safety, Tolerability and Pharmacokinetics of KAI-4169 in Hemodialysis Subjects with Secondary Hyperparathyroidism" NIH, U.S. National Library of Medicine, Study: NCT01134562, 6 pages (Latest Version Submitted 2017) Online article downloaded from https://clinicaltrials.gov/ct2/history/NCT01134562?A6&B6&C=.

(Continued)

*Primary Examiner* — Julie Ha
(74) *Attorney, Agent, or Firm* — McDermott Will & Emery LLP; Judy M. Mohr; Brennen P. Baylor

(57) ABSTRACT

A liquid formulation comprising a peptide agonist of the calcium sensing receptor and method of preparing and using the formulation are provided.

13 Claims, 13 Drawing Sheets

(56) References Cited

OTHER PUBLICATIONS

ClinicalTrials.gov archive, "Open-label Study to Asses the Long-Term Safety and Efficacy of AMG416 (Also Known as KAI-4169) in Patients with Secondary Hyperthyroidism" NIH, U.S. National Library of Medicine, Study: NCT01576146, 6 pages (Latest Version Submitted 2017) Online article downloaded from https://clinicaltrials.gov/ct2/history/NCT01576146?A=2&B=2&C=.

ClinicalTrials.gov archive, "Feb. 29, 2012: Asses the Efficacy and Safety of AMG416 in the Treatment of Secondary Hyperthyroidism (SHPT) in Subjeccts with Chronic Kidney Disease on Hemodialysis" NIH, U.S. National Library of Medicine, Study: NCT01785849, 14 pages (Latest Version Submitted 2019) Online article downloaded from https://clinicaltrials.gov/ct2/history/NCT01785849?A=3&B=3&C=.

Devrim, "Parenteral Preparations", Pharmaceutical Technology IV, Topic 1, Week 1, subject PHA486, Ankara Universitesi, 72 pages (Document created May 5, 2020) Online article downloaded from https://acikders.ankara.edu.tr/course/view.php?id=5752.

EMA: European Medicines Agency, "Note for Guidance on Stability Testing: Stability testing of New Drug Substances and Products", No. CPMP/ICH/2736/99, 20 pages (2003).

EMA: European Medicines Agency, "Assessment report: Parsibiv", No. EMEA/H/C/003995/000, 10 pages (2016).

Fukagawa et al., "Hyperthyroidism in chronic kidney disease patients: an update on current pharmacotherapy", Expert Opinion on Pharmacotherapy, vol. 14, No. 7, pp. 863-871 (2013).

Gad, (ed.), "Biotechnology-Derived Drug Product Development", Section 1.1, pp. 19-21, and "Liquid Dosage Forms", Section 4.3, pp. 330-333, Pharmaceutical Manufacturing Handbook: Production and Processes, Wiley-Interscience, John Wiley & Sons, Inc., (2008).

Hovgaard et al., (eds.), "Peptides and Proteins as Parenteral Solutions", Pharmaceutical Formulation Development of Peptides and Proteins, $2^{nd}$ Edition, CRC Press, pp. 155 (2013).

Ionova and Wilson, "Biologic Excipients: Importance of clinical awareness of inactive ingredients", PLoS One, vol. 15, No. 6, Article e0235076, 13 pages (2020).

Johnson and Besselsen, "Practical Aspects of Experimental Design in Animal Research", Ilar J., vol. 43, No. 4, pp. 202-206 (2002), Online article downloaded from https://doi.org/10.1093/ilar.43.4.202.

Stahl and Wermuth, (eds), "Pharmaceutical Salts", Handbook of Pharmaceutical Salts, Properties, Selection, and Use, $2^{nd}$ Edition, Wiley VCH, pp. 402-403 (2011).

Volkin et al., "Degradative Covalent Reactions Important to Protein Stability", Molecular Biotechnology, vol. 8, pp. 105-122 (1997).

Walter et al., "Pharmacology of AMG 416 (Velcalcetide), a Novel Peptide Agonist of the Calcium-Sensing Receptor, for the Treatment of Secondary Hyperparathyroidism in Hemodialysis Patients", JPET Fast Forward, jpet.113.204834, 53 pages (2013) Online Article downloaded from https://doi.org/10.1124/jpet.113.204834.

Walter et al., "Pharmacology of AMG 416 (Velcalcetide), a Novel Peptide Agonist of the Calcium-Sensing Receptor, for the Treatment of Secondary Hyperparathyroidism in Hemodialysis Patients", JPET, ASPET Journals, Evidence of Earlier Version of Article, 9 pages (2013) Online Article downloaded from https://jpet.aspetjournals.org/content/346/2/229/tab-article-info.

Acetic Acid, Calculation sheet showing that 0.2M acetic acid has a pH of 2.7, 1 page, Retreived Jun. 10, 2020.

"Actimmune® (Interferon gamma-1 b)", Prescribing Information, InterMune, Inc., 10 pages (2007).

AMG 416, Stability data, Primary Stability Batches, Tables 1-12, Amgen, Post filing data, pp. 3-15 (Accessed from the European Patent Register on Aug. 17, 2017).

Amgen, "Amgen Provides Update on Status of Parsabiv™ (Etelcalcetide) New Drug Application (NDA) Submitted to the U.S. Food and Drug Administration (FDA)", Amgen News Releases, pp. 1-7, Accessed Jan. 31, 2017.

Aulton, ed., "The Design and Manuafacture of Medicines", Aulton's Pharmaceutics, Third Edition, Churchill Livingstone Elsevier, Elsevier Limited, pp. 8, 368-369, and 616-620 (2007).

Avanti, "Innovative strategies for stabilization of therapeutic peptides in aqueous formulations", Ph.D. Thesis, Department of Pharmaceutical Technology and Biopharmacy, University of Groningen, 157 pages (2012).

Bastin et al., "Salt Selection and Optimization Procedures for Pharmaceutical Entities", Org. Proc. Res & Dev., vol. 4, No. 5, pp. 427-435 (2000).

Bauer et al., "Manual of Pharmaceutical Technology, With an introduction to biopharmaceuticals", Wissenschaftliche Verlagsgesellschaft mgH Stuttgart, Birkenwaldstraße 44, 70191 Stuttgart, Chapter 9, *Parenterals, including blood preparations, sera and vaccines*, pp. 238-243 (2006) German Language with English Translation.

Berge et al. "Pharmaceutical Salts", J. Pharm. Sci., vol. 66, No. 1, pp. 1-18 (1977).

Bi et al., "Effect of buffer pH, buffer concentration and skin with or without enzyme inhibitors on the stability of [$Arg^8$]-vasopressin", Int. J. Pharm., vol. 197, pp. 87-93 (2000).

*Biological buffers*; AppliChem, pp. 1-16 (2008).

Bontempo, "Development of Biopharmaceutical Parenteral Dosage Forms", Chapter 5, "Formulation Development", *Drugs and the Pharmaceutical Sciences*, Bontempo J.A., Ed., Marcel Dekker Inc., New York, vol. 85, pp. 109-142 (1997).

Chang et al., "Parenteral Formulations of Proteins and Peptides: Stability and Stabilizers", J Parent. Sci. Tech., vol. 42, No. 2S, Technical Report No. 10, pp. s4-s26 (1988).

Chang et al., "Lyophilized Biologics: Lyophilized Formulations", Lyophilized Biologics and Vaccines, Varshney and Singh, eds., Springer Science + Business Media, New York, pp. 93-119 (2015).

Chen et al., "Modification of Cysteine Residues In Vitro and In Vivo Affects the Immunogenicity and Antigenicity of Major Histocompatibility Complex Class I-Restricted Viral Determinants", *J. Exp. Med.*, vol. 189, No. 11, pp. 1757-1764 (1999).

Cleland et al., "Formulation and Delivery of Proteins and Peptides, Design and Development Strategies", *Formulation and Delivery of Proteins and Peptides*; Cleland and Langer, eds., ACS Symposium Series, American Chemical Society, Washington, DC, pp. 1-19 (1994).

"DDAVP® Injection, (desmopressin acetate)", Package Insert, Sanofi-Aventis US LLC, 9 pages (2007).

Epoetin alfa HEXAL®, "Solution for injection in a pre-filled syringe", HEXAL packaging leaflet, Diese Gebrauchsinformation wurde zultzt genehnight, 2 pages (2010) German Language with English Translation.

Etelcalcetide, Compound Summary, PubChem, pp. 1-60 (2020), Online article accessed from https://pubchem.ncbi.nlm.nih.gov/compound/Etelcalcetide.

EU Clinical Trials Register "A Randomized, Double-blind, Placebo-controlled, Phase 3, Study to Assess the Efficacy and Safety of AMG 416 in the Treatment of Secondary Hyperparathyroidism in Subjects With Chronic Kidney Disease", EudraCT No. 2012-002805-23, Sponsor Protocol No. 20120229(KAI-4169-006), 1 page, start date: Jan. 22, 2013.

European Medicines Agency, "Parsabiv, International non-proprietary name: etelcalcetide", EMA/664198/2016, Committee for Medicinal Products for Human USE (CHMP), Assessment Report, Procedure No. EMEA/H/C/003995/000, pp. 1-98 Sep. 15, 2016.

Feltkamp et al., "Pharmaceutical Quality Control", Work Methods of the Pharmaceutical Industry, Sucker and Fuchs, Georg Thieme Verlag Stuttgart, New York, vol. 3, pp. 502-504 (1983) *German Language with English Translation*.

Foreman and Lawrence, "Induction of Histamine Secretion by Polycations", Biochimica Et Biophysica Acta, vol. 629, No. 3, pp. 587-603 (1980).

Frokjaer and Hovgaard, "Pharmaceutical Formulation Development of Peptides and Proteins", Taylor & Francis Limited, 11 New Fetter Lane, London EC4P 4EE, Chapter 8, *Peptides and Proteins as Parental Solutions*, Akers and DeFelippis, pp. 145-155 (2000).

(56) References Cited

OTHER PUBLICATIONS

Haack and Beck-Sickinger, "Multiple Peptide Synthesis to Identify Bioactive Hormone Structures", Top. Curr. Chem., vol. 278, pp. 243-288 (2007).

Hancock and Chapple, "Peptide Antibiotics." Antimicrobial Agents and Chemotherapy, vol. 43, No. 6, pp. 1317-1323 (1999).

He et al., "Synthesis and chemical stability of a disulfide bond in a model cyclic pentapeptide: Cyclo(1,4)-Cys-Gly-Phe-Cys-Gly-OH", J. Pharm. Sci., vol. 95, No. 10, pp. 2222-2234 (2006).

Himmelfarb et al.,eds., "Chronic Kidney Disease, Dialysis, and Transplantation", 3$^{rd}$ Edition, Saunders Elsevier, 1600 John F. Kennedy Blvd., Ste 1800, Philidelphia, PA 19103-2899, pp. 92-93, 112, 335, and 349-352 (2010).

Hochgrafe et al., "S-Cysteinylation Is a General Mechanism for Thiel Protection of Bacillus subtilis Proteins after Oxidative Stress", J. Biol. Chem., vol. 282, No. 36, pp. 25981-25985 (2007).

Hong et al., "Effect of D-Amino Acid Substitution on the Stability, the Secondary Structure, and the Activity of Membrane-Active Peptide", Biochem Pharmacol., vol. 58, No. 11, pp. 1775-1780 (1999).

Hruby, "Designing Peptide Receptor Agonists and Antagonists", Nat. Rev. Drug Dis., vol. 1, pp. 847-858 (2002).

Integrilin (eptifibatide), Highlights of prescribing information, Initial U.S. Approval: 1998, Reference ID: 3281355, 16 pages (Revised 2013).

International Preliminary Report on Patentability and Written Opinion of the International Searching Authority from PCT Patent Application No. PCT/US2014/044622 dated Dec. 29, 2015.

International Search Report from PCT Patent Application No. PCT/US2014/044622 dated Sep. 24, 2014, Application now published as International Publication No. WO2014/210489 on Dec. 31, 2014.

Jacob et al., "Stability of Proteins in Aqueous Solution and Solid State", Ind .J. Pharm. Sci., pp. 154-163 (2006).

Lachman et al., "The Theory and Practice of Industrial Pharmacy", 3$^{rd}$ Edition, Indian Edition, Varghese Publishing House, Hind Rajasthan Building, Dadar Bombay 400 014, pp. 190-195 and 764-768 (1987).

Miller et al., "Comparison of the Proteolytic Susceptibilities of Homologous L-Amino Acid, D-Amino Acid, and N-Substituted Glycine Peptide and Peptoid Oligomers", Drug Dev. Res., vol. 35, pp. 20-32 (1995).

Moe and Drueke, "Management of Secondary Hyperparathyroidism: The Importance and the Challenge of Controlling Parathyroid Hormone Levels without Elevating Calcium, Phosphorus, and Calcium-Phosphorus Product", Am. J. Nephrol, vol. 23, pp. 369-379 (2003).

Morrison and Weiss, "Combinatorial alanine-scanning", Curr. Opin. Chem. Biol., vol. 5, pp. 302-307 (2001).

Nam et al., "Alanine Scan of [L-Dap2]Ramoplanin A2 Aglycon: Assessment of the Importance of Each Residue", J. Am Chem Soc., vol. 129, No. 28, pp. 8747-8755 (2007).

Neau, "Pharmaceutical Salts", *Water-Insoluble Drug Formulation*, Liu, ed., Interpharm Press, Colorado, pp. 405-425 (2000).

Notice of Opposition against European Patent No. EP3013318B1 "Stable liquid formulation of AMG 416 (Velcalcetide)", dated Jan. 19, 2018 in the name and on behalf of Hexal AG, 30 pages (2018).

Olgaard et al., eds., "The Spectrum of Mineral and Bone Disorders in Chronic Kidney Disease", 2$^{nd}$ Edition, Oxford University Press, Great Clarendon Street, Oxford ox2 6dp, Chapter 26, *Calcimimetics and calcilytics in the treatment of chronic kidney disease-mineral and bone disorder*, Nemeth, pp. 443-444 (2010).

"Oxytocin Injection USP Synthetic", Package Insert, SICOR Pharmaceuticals, Inc., 6 pages (2006).

Parsabiv etelcalcetide, Summary of opinion (initial authorization), European Medicines Agency, Committee for Medicinal Products for Human Use (CHMP), London, United Kingdom, 4 pages, (2016).

Patel et al., "Stability Considerations for Biopharmaceuticals, Overview of Protein and Peptide Degradation Pathways", Bioprocess International, 25 pages (2011).

Pegorier et al., "Eosinophil-Derived Cationic Proteins Activate the Synthesis of Remodeling Factors by Airway Epithelial Cells", J. Immunol., vol. 177, pp. 4861-4869 (2006).

Pujals et al., "d-SAP: A New, Noncytotoxic, and Fully Protease Resistant Cell-Penetrating Peptide", ChemMedChem, vol. 3, pp. 296-301 (2008).

Rossi and Leroux, "Chapter 4: Principles in the Development of Intravenous Lipid Emulsions", Role of Lipid Excipients in Modifying Oral and Parenteral Drug Delivery, Basic Principles and Biological Examples, Wasan, Ed., Wiley-Interscience, A John Wiley & Sons, Inc. Publication, pp. 88-123 (2007).

"Sandostatin® (octreotide acetate) Injection", Package Insert, Novartis Pharmaceuticals Corporation, 12 pages (2002).

Sek, "Breaking Old Habits: Moving Away From Commonly Used Buffers in Pharmaceuticals", Eur. Pharm. Rev., Issue 3, 12 pages (2012).

Shen et al., "A pharmacokinetic/pharmacodynamic model for AMG 416, a novel calcimimetic peptide, following a single intravenous dose in healthy subjects", J. Clin. Pharmacol., vol. 54, No. 10, pp. 1125-1133 (2014).

Specification of European Patent Application No. 09163237.2, "Liquid hand washing detergent composition", 23 pages, Filed Jun. 19, 2009.

Summons to attend oral proceedings pursuant to Rule 115(1) EPC in European Patent Application No. 14742093.9, 13 pages, mailed Sep. 26, 2018.

Tugyi et al., "Partial D-amino acid substitution: Improved enzymatic stability and preserved Ab recognition of a MUC2 epitope peptide", PNAS, vol. 102, No. 2, pp. 413-418 (2005).

Ugwu and Apte, "The Effect of Buffers on Protein Conformational Stability", Pharmaceutical Technology, pp. 86-113 (2004).

Van Nispin, "Chemical and physical stability of peptides", Topics in Pharmaceutical Sciences, Proceedings of the 47$^{th}$ International Congress of Pharmaceutical Sciences of F.I.P., Amsterdam, Netherlands, Aug. 31 to Sep. 4, pp. 293-307 (1987).

Van Regenmortel Muller, "D-peptides as immunogens and diagnostic reagents", Curr Op. Biotech., vol. 9, pp. 377-382 (1998).

Voet and Voet, "Biochemistry", Joun Wiley & Sons, Inc., Authorized translation from the English language edition, Chapter 4, p. 60, Table 4-2 (1990) German Language.

Voet and Voet, "Biochemistry", *Acids, bases and buffer systems*, Translation published by Maelicke and Müller-Esterl, VCH Verlagsgesellschaft mbH, D-69451 Weinheim, Bundesrepublik Deutschland, pp. 35-41 (1994) German Language with English Translation.

Wall, "Disulfide bonds: determination, location, and influence on molecular properties of proteins", J. Agric. Food Chem., vol. 19, No. 4, pp. 619-625 (1971).

Walter et al., "Pharmacology of AMG 416 (Velcalcetide), a Novel Peptide Agonist of the Calcium-Sensing Receptor, for the Treatment of Secondary Hyperparathyroidism in Hemodialysis Patients", J. Pharmacol. Exp. Ther., vol. 346, pp. 229-240 (2013).

Wang and Hanson, "Parenteral Formulations of Proteins and Peptides: Stability and Stabilizers", J. of Parenteral Science and Technology, Supplement, vol. 42, pp. s4-s26 (1988).

Wong et al., "Suspensions for intravenous (IV) injection: A review of development preclinical and clinical aspects", Adv. Drug Del. Rev., vol. 60, pp. 939-954 (2008).

Zheutlin et al., "Stimulation of Basophil and Rat Mast Cell Histamine Release by Eosinophil Granulate-Derived Cationic Proteins", J. Immunol., vol. 133, No. 4, pp. 2180-2186 (1984).

Zhou et al. "Biologics formulation factors affecting metal leachables from stainless steel", AAPS PharmSciTech, vol. 12, No. 1, pp. 411-421 (2011).

Zhu and Wang, "Formulation of protein-and paptide-based parenteral products", *Pharmaceutical Dosage Forms: Parenteral Medications*, Third Edition, vol. 1: Formulation and Packaging; Nema and Ludwig, eds., Informa Healthcare, New York, pp. 222-253 (2010).

Amgen, "Efficacy and Safety of Etelcalcetide (AMG 416) in the Treatment of Secondary Hyperparathyroidism (SHPT) in Patients With Chronic Kidney Disease on Hemodialysis", NIH, U.S. National Library of Medicine, ClinicalTrials.gov, Results First Posted Mar.

(56) References Cited

OTHER PUBLICATIONS 27, 2017, Last updated Aug. 26, 2019, Online article retrieved from https://clinicaltrials.gov/ct2/show/study/NCT01785849 (2017).
Powell, "Peptide Stability in Aqueous Parental Formulations, Prediction of Chemical Stability Based on Primary Sequence", Formulation and Delivery of Proteins and Peptides, ACE Symposium Series, vol. 567, Chapter 7, pp. 100-117 (1994).

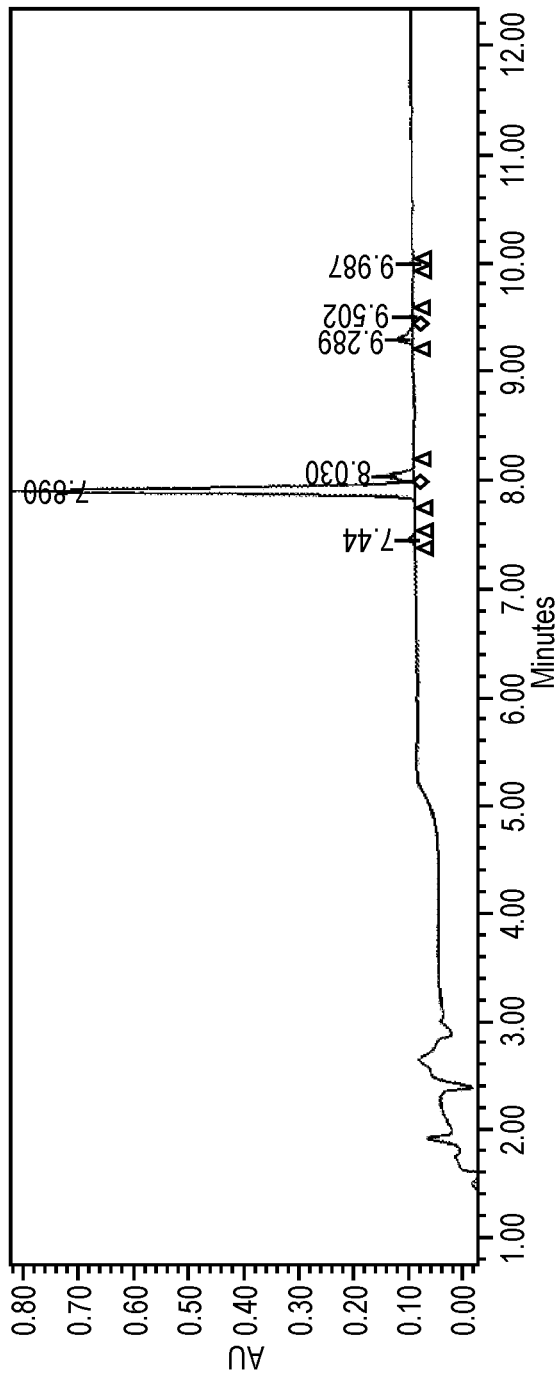
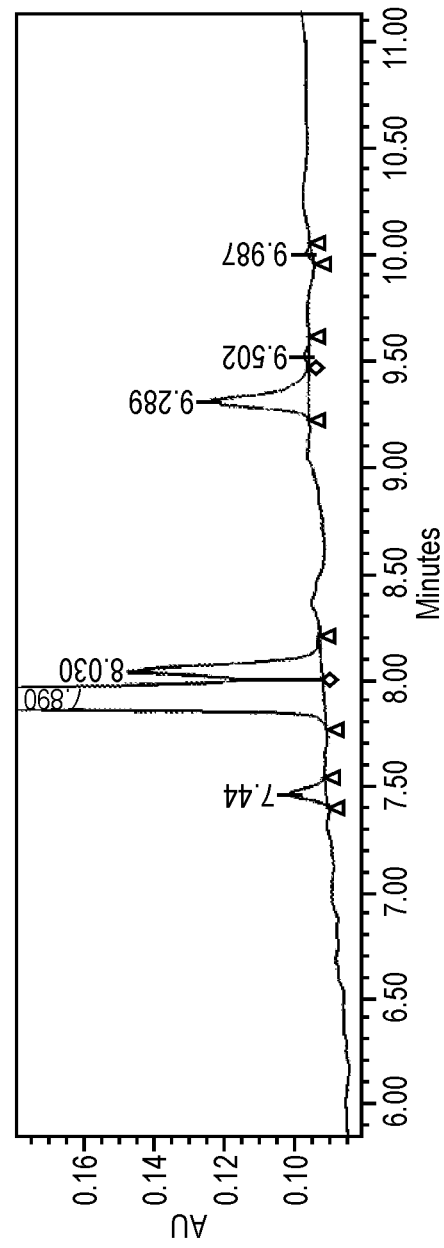

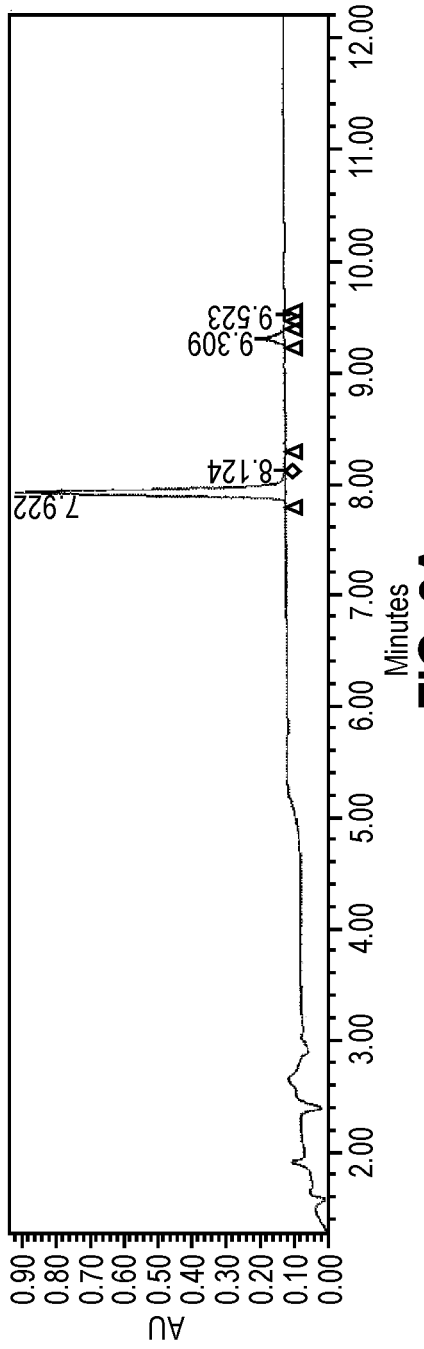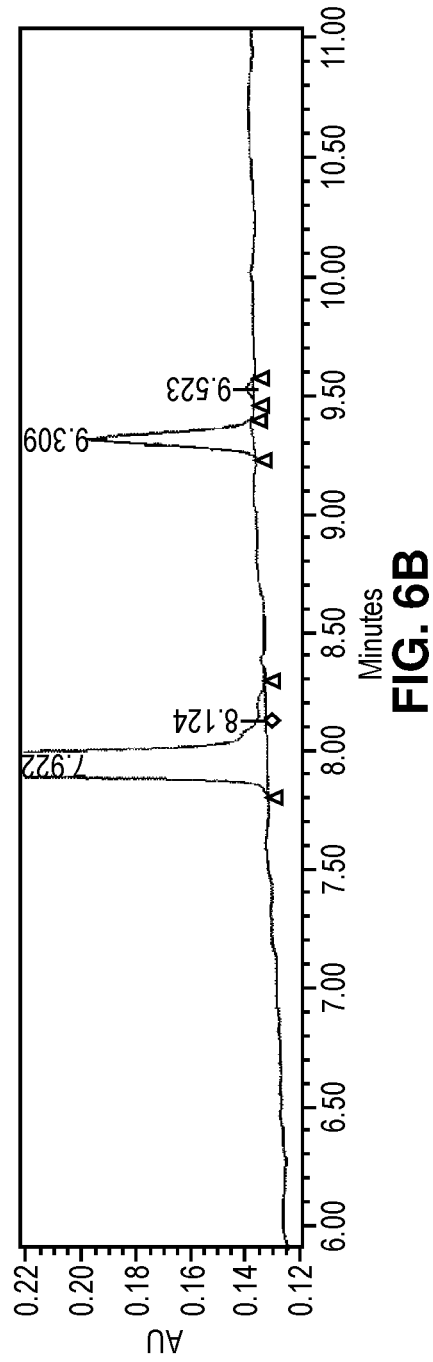
FIG. 6A
FIG. 6B

STABLE LIQUID FORMULATION OF AMG 416 (ETELCALCETIDE)

CROSS-REFERENCE TO RELATED APPLICATIONS

This application is a continuation of U.S. application Ser. No. 16/430,322, filed Jun. 3, 2019, now allowed, which is a continuation of U.S. application Ser. No. 15/802,390, filed Nov. 2, 2017, now U.S. Pat. No. 10,344,765, which is a continuation of U.S. application Ser. No. 14/908,481, filed Jan. 28, 2016, now U.S. Pat. No. 9,820,938, which is a U.S. National Stage of International Patent Application No. PCT/US2014/044622, filed Jun. 27, 2014, which claims the benefit of U.S. Provisional Application No. 61/840,618, filed Jun. 28, 2013, the contents of each is incorporated herein by reference in its entirety.

FIELD OF THE INVENTION

The present disclosure relates to a liquid formulation comprising a peptide agonist of the calcium sensing receptor, particularly to such a formulation that remains stable after storage for an extended period. The disclosure is also directed to methods of preparing and using the formulation.

BACKGROUND OF THE INVENTION

A variety of compounds having activity for lowering parathyroid hormone levels have been described. See International Publication No. WO 2011/014707. In one embodiment, the compound may be represented as follows:

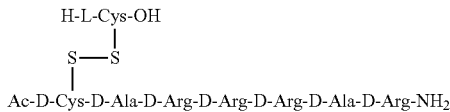

The main chain has 7 amino acids, all in the D-configuration and the side-chain cysteine residue is in the L-configuration. The amino terminal is acetylated and the carboxyl-terminal is amidated. This compound ("AMG-416") has utility for the treatment of secondary hyperparathyroidism (SHPT) in hemodialysis patients. A liquid formulation comprising AMG-416 may be administered to a subject intravenously. The hydrochloride salt of AMG-416 may be represented as follows:

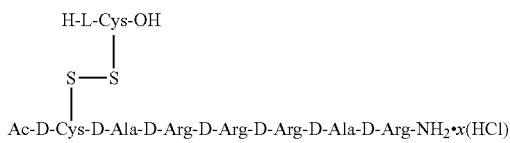

Therapeutic peptides pose a number of challenges with respect to their formulation. Peptides in general, and particularly those that contain a disulfide bond, typically have only moderate or poor stability in aqueous solution. Peptides are prone to amide bond hydrolysis at both high and low pH. Disulfide bonds can be unstable even under quite mild conditions (close to neutral pH). In addition, disulfide containing peptides that are not cyclic are particularly prone to dimer formation. Accordingly, therapeutic peptides are often provided in lyophilized form, as a dry powder or cake, for later reconstitution. A lyophilized formulation of a therapeutic peptide has the advantage of providing stability for long periods of time, but is less convenient to use as it requires the addition of one or more diluents and there is the potential risk for errors due to the use of an improper type or amount of diluent, as well as risk of contamination. In addition, the lyophilization process is time consuming and costly.

Accordingly, there is a need for an aqueous liquid formulation comprising a peptide agonist of the calcium sensing receptor, such as AMG 416. It would be desirable for the liquid formulation to remain stable over a relevant period of time under suitable storage conditions and to be suitable for administration by intravenous or other parenteral routes.

SUMMARY OF THE INVENTION

A liquid formulation comprising a peptide agonist of the calcium sensing receptor, such as AMG 416 is provided.

In one embodiment, the formulation has a pH of about 2.0 to about 5.0. In another embodiment, the formulation has a pH of 2.5 to 4.5. In another embodiment, the formulation has a pH of 2.5 to 4.0. In another embodiment, the formulation has a pH of 3.0 to 3.5. In another embodiment, the formulation has a pH of 3.0 to 4.0. In another embodiment, the formulation has a pH of 2.8 to 3.8.

In another embodiment, the pH of the formulation is maintained by a pharmaceutically acceptable buffer. Such buffers include, without limitation, succinate buffers, acetate buffers, citrate buffers and phosphate buffers. In another embodiment, the buffer is succinate buffer. The pH of the formulation may be adjusted as needed with an acid or base, such as HCl or NaOH.

In another embodiment, the peptide agonist of the calcium sensing receptor is present at a concentration of 0.1 mg/mL to 20 mg/mL. In another embodiment, the peptide is present at a concentration of 1 mg/mL to 15 mg/mL. In another embodiment, the peptide is present at a concentration of 2.5 mg/mL to 10 mg/mL. In another embodiment, the peptide is present at a concentration of about 1 mg/mL, about 5 mg/mL or about 10 mg/mL.

In another embodiment, AMG 416 is present at a concentration of about 0.1 mg/mL to about 20 mg/mL. In one embodiment, AMG 416 is present at a concentration of about 1 mg/mL to about 15 mg/mL. In another embodiment, AMG 416 is present at a concentration of about 2.5 mg/mL to about 10 mg/mL. In another embodiment, AMG 416 is present at a concentration of about 1 mg/mL, about 2.5 mg/mL, about 5 mg/mL or about 10 mg/mL.

In another embodiment, AMG 416 is present at a concentration of 0.1 mg/mL to 20 mg/mL. In one embodiment, AMG 416 is present at a concentration of 1 mg/mL to 15 mg/mL. In another embodiment, AMG 416 is present at a concentration of 2.5 mg/mL to 10 mg/mL. In another embodiment, AMG 416 is present at a concentration of 1 mg/mL to 5 mg/mL. In another embodiment, AMG 416 is present at a concentration of 5 mg/mL to 10 mg/mL. In another embodiment, AMG 416 is present at a concentration of 0.5 to 1.5 mg/mL, 2.0 to 3.0 mg/mL, 4.5 to 5.5 mg/mL or 9.5 to about 10.5 mg/mL.

In another embodiment, the formulation further comprises a pharmaceutically acceptable tonicity modifier or mixture of pharmaceutically acceptable tonicity modifiers. In another embodiment, the tonicity modifier (or mixture of tonicity modifiers) is present at a concentration sufficient for the formulation to be approximately isotonic with bodily fluids (e.g., human blood). In another aspect, the tonicity modifier is NaCl.

In another embodiment, the formulation comprises a therapeutically effective amount of a peptide agonist of the calcium sensing receptor. In a preferred embodiment, the formulation comprises a therapeutically effective amount of AMG 416.

In another embodiment, the formulation has less than 10% degradation when stored at 2-8° C. for up to 2 years. In another embodiment, the formulation has less than 10% degradation when stored at 2-8° C. for up to 3 years. In another embodiment, the formulation has less than 10% degradation when stored at 2-8° C. for up to 4 years.

In another embodiment, the formulation has less than 8% degradation when stored at 2-8° C. for up to 2 years. In another embodiment, the formulation has less than 8% degradation when stored at 2-8° C. for up to 3 years. In another embodiment, the formulation has less than 8% degradation when stored at 2-8° C. for up to 4 years.

In another embodiment, the formulation has less than 10% degradation when stored at room temperature for 3 months. In another embodiment, the formulation has less than 10% degradation when stored at room temperature for up to 6 months. In another embodiment, the formulation has less than 10% degradation when stored at room temperature for up to 1 year.

In another embodiment, a formulation comprising 0.5 mg/mL to 20 mg/mL of a peptide agonist of the calcium sensing receptor (e.g., AMG 416) in aqueous solution, a succinate buffer that maintains the formulation at a pH of about 3.0 to about 3.5, and a sufficient concentration of sodium chloride for the formulation to be approximately isotonic with human blood is provided.

BRIEF DESCRIPTION OF THE DRAWINGS

FIG. 1A shows the stability of AMG 416 solutions having concentrations of 200, 66, 20, 6.7, 2.2 and 0.67 mg/mL of AMG 416. In FIG. 1B, the scale is expanded to more clearly illustrate the degradation pattern at concentrations of 20 mg/mL and below.

In FIG. 3A, the concentration of AMG 416 is 10 mg/mL and in FIG. 3B the concentration of AMG 416 is 2.5 mg/mL.

In FIG. 4A, the concentration of AMG 416 is 10 mg/mL and in FIG. 4B the concentration of AMG 416 is 2.5 mg/mL.

FIGS. 5A-5B are HPLC chromatograms. The HPLC trace in FIG. 5A is for a AMG 416 solution (5 mg/mL, pH 2.25) stored for 27 days at 40° C. (87.8% purity). In FIG. 5B, the scale is expanded to more clearly illustrate the peaks.

FIGS. 6A-6B are HPLC chromatograms. The HPLC trace in FIG. 6A is for a AMG 416 solution (5 mg/mL, pH 3.5) stored for 27 days at 40° C. (91.7% purity). In FIG. 6B, the scale is expanded to more clearly illustrate the peaks.

(FIG. 10A), RT (FIG. 10B) and at 40° C. (FIG. 10C). Note that the scale of the y-axis is different in each graph.

(FIG. 11A), RT (FIG. 11B) and at 40° C. (FIG. 11C). Note that the scale of the y-axis of FIG. 11C is different from that in FIGS. 11A and 11B.

(FIG. 12A), 25° C. (FIG. 12B) and 40° C. (FIG. 12C).

(FIG. 13A), 25° C. (FIG. 13B) and 40° C. (FIG. 13C).

DETAILED DESCRIPTION OF THE INVENTION

Figure 1A:
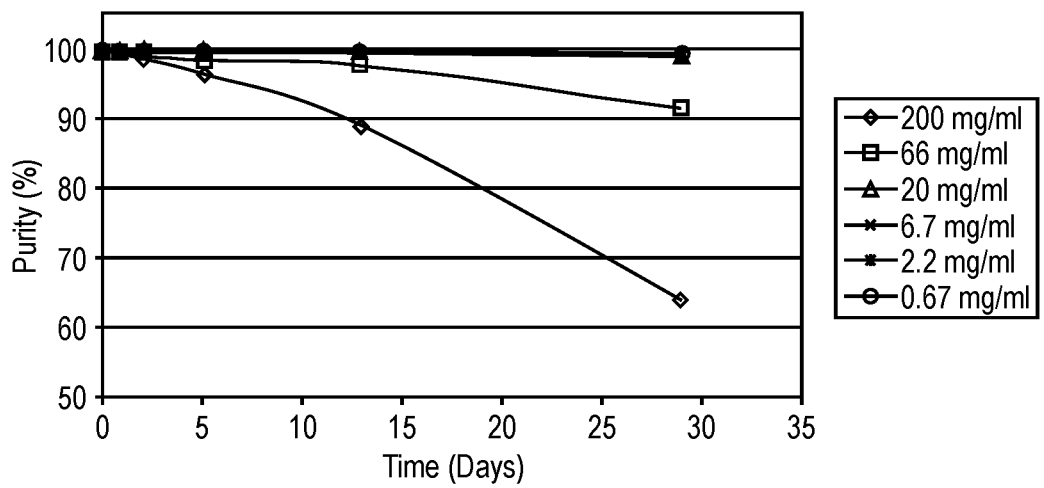
FIGS. 1A-1B are graphs plotting purity (%) as a function of time (days) for AMG 416 solutions in succinate-buffered saline (pH 4.5) at room temperature (RT).

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, molecular biology and protein chemistry described herein are those well known and commonly used in the art. The methods and techniques of the present application are generally performed according to conventional methods well known in the art and as described in various general and more specific references that are cited and discussed throughout the present specification unless otherwise indicated. See, e.g., Laszlo, Peptide-Based Drug Design: Methods and Protocols, Humana Press (2008); Benoiton, Chemistry of Peptide Synthesis, CRC Press (2005); Ausubel et al., Current Protocols in Molecular Biology, Greene Publishing Associates (1992), which are incorporated herein by reference for any purpose. Purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this disclosure is not limited to the particular methodology, protocols, and reagents, etc., described herein and as such may vary. The terminology used herein is for the purpose of describing particular embodiments only, and is not intended to limit the scope of the disclosed, which is defined solely by the claims.

As used herein, the term "about" in the context of a given value or range refers to a value or range that is within 20%, preferably within 10%, and more preferably within 5% of the given value or range I. General Definitions Following convention, as used herein "a" and "an" mean "one or more" unless specifically indicated otherwise.

The term "AMG 416" refers to the compound having the chemical name: N-acetyl-D-cysteinyl-D-alanyl-D-arginyl-D-arginyl-D-arginyl-D-alanyl-D-arginamide disulfide with L-cysteine, which may be represented as:

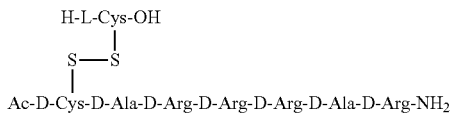

The terms "AMG 416 hydrochloride" or "AMG 416 HCl" are interchangeable and refer to the compound having the chemical name: N-acetyl-D-cysteinyl-D-alanyl-D-arginyl-D-arginyl-D-arginyl-D-alanyl-D-arginamide disulfide with L-cysteine hydrochloride, which may be represented as:

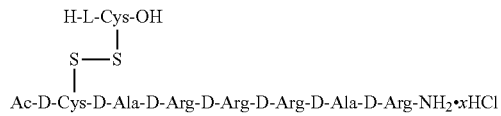

As used herein, the terms "amino acid" and "residue" are interchangeable and, when used in the context of a peptide or polypeptide, refer to both naturally occurring and synthetic amino acids, as well as amino acid analogs, amino acid mimetics and non-naturally occurring amino acids that are chemically similar to the naturally occurring amino acids.

The term "treating" refers to any indicia of success in the treatment or amelioration of an injury, pathology or condition, including any objective or subjective parameter such as abatement; remission; diminishing of signs or symptoms or making the injury, pathology or condition more tolerable to the patient; slowing in the rate of degeneration or decline; making the final point of degeneration less debilitating; improving a patient's physical or mental well-being. The treatment or amelioration of signs or symptoms can be based on objective or subjective parameters; including the results of a physical examination, for example, the treatment of SHPT by decreasing elevated levels of parathyroid hormone (PTH).

The terms "therapeutically effective dose" and "therapeutically effective amount," as used herein, means an amount that elicits a biological or medicinal response in a tissue system, animal, or human being sought by a researcher, physician, or other clinician, which includes alleviation or amelioration of the signs or symptoms of the disease or disorder being treated, for example, an amount of AMG 416 that elicits a desired reduction in elevated PTH level.

The term "room temperature" as used herein refers to a temperature of about 25° C. Storage under "refrigerated conditions" as used herein refers to storage at a temperature of 2-8° C.

The terms "peptide", "polypeptide" and "protein" are interchangeable and refer to a polymer of amino acids, typically joined together through peptide or disulfide bonds. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Peptides, polypeptides and proteins can be produced by a liquid-phase synthesis or solid phase synthesis or by a genetically-engineered or recombinant cell.

A "variant" of a peptide or polypeptide comprises an amino acid sequence wherein one or more amino acid residues are inserted into, deleted from and/or substituted into the amino acid sequence relative to another polypeptide sequence. Variants include fusion proteins.

A "derivative" of a peptide or polypeptide is a peptide or polypeptide that has been chemically modified in some manner distinct from insertion, deletion, or substitution variants, e.g., via conjugation to another chemical moiety. Such modification can include the covalent addition of a group to the amino and/or carboxy termini of the peptide or polypeptide, e.g., acetylation of the amino terminus and/or amidation of the carboxy terminus of a peptide or polypeptide.

The term "amino acid" includes its normal meaning in the art. The twenty naturally-occurring amino acids and their abbreviations follow conventional usage. See, Immunology-A Synthesis, 2nd Edition, (E. S. Golub and D. R. Green, eds.), Sinauer Associates: Sunderland, Mass. (1991), which is incorporated herein by reference for any purpose. Stereoisomers (e.g., d-amino acids) of the 19 conventional amino acids (except glycine), unnatural amino acids such as [alpha]-, [alpha]-disubstituted amino acids, N-alkyl amino acids, and other unconventional amino acids may also be suitable components for polypeptides and are included in the phrase "amino acid." Examples of unconventional amino acids include: homocysteine, ornithine, 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the amino terminal is to the left and the carboxyl-terminal is to the right, in accordance with standard usage and convention.

A "subject" or "patient" as used herein can be any mammal. In a typical embodiment, the subject or patient is a human.

A "buffer" as used herein refers to a composition, wherein the composition comprises a weak acid and its conjugate base (usually as a conjugate base salt), a weak base and its conjugate acid, or mixtures thereof. Those skilled in the art would readily recognize a variety of buffers that could be used in the formulations used in the invention. Typical buffers include, but are not limited to pharmaceutically acceptable weak acids, weak bases, or mixtures thereof. Exemplary pharmaceutically acceptable buffers include acetate (e.g., sodium acetate), succinate (e.g., sodium succinate).

The phrase "weak acid" is a chemical acid that does not fully ionize in aqueous solution; that is, if the acid is represented by the general formula HA, then in aqueous solution A− forms, but a significant amount of undissociated HA still remains. The acid dissociation constant (Ka) of a weak acid varies between 1.8×10-16 and 55.5.

The phrase "weak base" is a chemical base that does not fully ionize in aqueous solution; that is, if the base was represented by the general formula B, then in aqueous solution BH+ forms, but a significant amount of unprotonated B still remains. The acid dissociation constant (Ka) of the resultant conjugate weak acid BH+ varies between 1.8×10-16 and 55.5.

The phrase "conjugate acid" is the acid member, HX+, of a part of two compounds (HX+, X) that transform into each other by gain or loss of a proton.

The phrase "conjugate base" is the base member, X−, of a pair of two compounds (HX, X−) that transform into each other by gain or loss of a proton.

The phrase "conjugate base salt" is the ionic salt comprising a conjugate base, X−, and a positively charged counterion.

The phrase "buffer system" means a mixture containing at least two buffers.

The term "q.s." means adding a quantity sufficient to achieve a desired function, e.g., to bring a solution to the desired volume (i.e., 100%).

The phrase "tonicity modifier" means a pharmaceutically acceptable inert substance that can be added to the formulation to adjust the tonicity of the formulation. Tonicity modifiers suitable for this invention include, but are not limited to, sodium chloride, potassium chloride, mannitol or glycerin and other pharmaceutically acceptable tonicity modifier.

II. Embodiments

The present disclosure relates to liquid formulations comprising a peptide agonist of the calcium sensing receptor, wherein the formulation has a pH of about 2.0 to about 5.0. In a preferred embodiment, the present disclosure relates to a liquid formulation comprising AMG 416, wherein the formulation has a pH of about 2.0 to about 5.0. AMG 416 and its preparation are described in International Pat. Publication No. WO 2011/014707. For example, AMG 416 may be assembled by solid-phase synthesis from the corresponding Fmoc-protected D-amino acids. After cleavage from the resin, the material may be treated with Boc-L-Cys(NPyS)—OH to form the disulfide bond. The Boc group may then be removed with trifluoroacetic acid (TFA) and the resulting product purified by reverse-phase high pressure liquid chromatography (HPLC) and isolated as the TFA salt form by lyophilization. The TFA salt can be converted to a pharmaceutically acceptable salt by carrying out a subsequent salt exchange procedure. Such procedures are well known in the art and include, e.g., an ion exchange technique, optionally followed by purification of the resultant product (for example by reverse phase liquid chromatography or reverse osmosis).

The formulations disclosed herein are described primarily in terms of the therapeutic peptide, AMG 416, as the active ingredient. However, as the skilled artisan will readily appreciate, the present disclosure also extends to variants and derivatives of AMG 416.

For example, in one embodiment, the disclosed formulations also may be used with: N-acetyl-D-cysteinyl-D-alanyl-D-arginyl-D-arginyl-D-arginyl-D-alanyl-D-arginamide disulfide with D-cysteine. In another embodiment, the disclosed formulation may also be used with N-acetyl-D-cysteinyl-D-alanyl-D-arginyl-D-arginyl-D-arginyl-D-alanyl-D-arginamide disulfide with N-acetyl-D-cysteine. In another embodiment, the disclosed formulations also may be used with: N-acetyl-D-cysteinyl-D-alanyl-D-arginyl-D-arginyl-D-arginyl-D-alanyl-D-arginamide disulfide with N-acetyl-L-cysteine.

In another embodiment, the disclosed formulations also may be used with: N-acetyl-l-cysteinyl-l-alanyl-l-arginyl-l-arginyl-l-arginyl-l-alanyl-l-arginamide disulfide with d-cysteine. In another embodiment, the disclosed formulations also may be used with: N-acetyl-l-cysteinyl-l-alanyl-l-arginyl-l-arginyl-l-arginyl-l-alanyl-l-arginamide disulfide with l-cysteine. In another embodiment, the disclosed formulations also may be used with: N-acetyl-l-cysteinyl-l-alanyl-l-arginyl-l-arginyl-l-arginyl-l-alanyl-l-arginamide disulfide with N-acetyl-d-cysteine. In another embodiment, the disclosed formulations also may be used with: N-acetyl-l-cysteinyl-l-alanyl-l-arginyl-l-arginyl-l-arginyl-l-alanyl-l-arginamide disulfide with N-acetyl-l-cysteine.

In another embodiment, the disclosed formulations also may be used with: N-acetyl-d-cysteinyl-d-arginyl-d-arginyl-d-alanyl-d-arginyl-d-alanyl-d-arginamide disulfide with d-cysteine. In another embodiment, the disclosed formulations also may be used with: N-acetyl-d-cysteinyl-d-arginyl-d-arginyl-d-alanyl-d-arginyl-d-alanyl-d-arginamide disulfide with l-cysteine. In another embodiment, the disclosed formulations also may be used with: N-acetyl-d-cysteinyl-d-arginyl-d-arginyl-d-alanyl-d-arginyl-d-alanyl-d-arginamide disulfide with N-acetyl-d-cysteine. In another embodiment, the disclosed formulations also may be used with: N-acetyl-d-cysteinyl-d-arginyl-d-arginyl-d-alanyl-d-arginyl-d-alanyl-d-arginamide disulfide with N-acetyl-l-cysteine.

In another embodiment, the disclosed formulations also may be used with: N-acetyl-l-cysteinyl-l-arginyl-l-arginyl-l-alanyl-l-arginyl-l-alanyl-l-arginamide disulfide with d-cysteine. In another embodiment, the disclosed formulations also may be used with: N-acetyl-l-cysteinyl-l-arginyl-l-arginyl-l-alanyl-l-arginyl-l-alanyl-l-arginamide disulfide with l-cysteine. In another embodiment, the disclosed formulations also may be used with: N-acetyl-l-cysteinyl-l-arginyl-l-arginyl-l-alanyl-l-arginyl-l-alanyl-l-arginamide disulfide with N-acetyl-d-cysteine. In another embodiment, the disclosed formulations also may be used with: N-acetyl-l-cysteinyl-l-arginyl-l-arginyl-l-alanyl-l-arginyl-l-alanyl-l-arginamide disulfide with N-acetyl-l-cysteine.

In another embodiment, the disclosed formulations also may be used with one or more of the compounds provided in Table 1, Table 2, Table 3, Table 4, Table 5, Table 6, Table 7, Table 8, Table 9 and/or Table 10 of International Pat. Publication No. WO 2011/014707. In another embodiment, the disclosed formulations may also be used with one or more of the compounds described in International Pat. Publication No. WO 2011/014707.

In some embodiments, the formulation contains a therapeutically effective amount of the active ingredient (e.g., AMG 416). A therapeutically effective amount of the active ingredient in any given embodiment of the formulation of the present disclosure will depend upon the volume of the formulation to be delivered to a given subject, as well as the age and weight of the subject, and the nature of the illness or disorder being treated. Depending on the dosage form, in some instances a therapeutically effective amount may be provided to the patient in one administration while in other instances a plurality of administrations may be required.

The liquid formulation of the present disclosure is a pharmaceutical composition suitable for administration by intravenously, intra-arterially, intramuscularly, and subcutaneously. In a preferred embodiment, the liquid formulation is suitable for administration by intravenous or other parenteral routes. Preferably, the liquid formulation is a sterile, aqueous solution. Typically, the solvent is injectable grade water or a mixture of water and one or more other water-miscible solvents(s), such as propylene glycol, polyethylene glycol, and ethanol. The use of sterile, deionized water as solvent is preferred. Other solvents which are suitable and conventional for pharmaceutical preparations can, however, be employed.

The formulation typically contains about 0.1 mg/mL to about 100 mg/mL of the active ingredient (e.g., AMG 416), about 0.1 mg/mL to about 20 mg/mL of the active ingredient, about 0.5 mg/mL to about 15 mg/mL of the active ingredient, about 1 mg/mL to about 10 mg/mL of the active ingredient, or about 2 mg/mL to about 5 mg/mL of the active ingredient. In some embodiments, the formulation contains about 1 mg/mL of the active ingredient, about 2 mg/mL of the active ingredient, about 2.5 mg/mL of the active ingredient, about 5 mg/mL of the active ingredient, about 10 mg/mL of the active ingredient or about 20 mg/mL of the active ingredient. In another embodiment, the formulation contains 0.1 mg/mL to 100 mg/mL of the active ingredient, 0.1 mg/mL to 20 mg/mL of the active ingredient, 0.5 mg/mL to 15 mg/mL of the active ingredient, or 1 mg/mL to 10 mg/mL of the active ingredient, or 2 mg/mL to 5 mg/mL of the active ingredient. In a preferred embodiment, the formulation contains 1 mg/mL to 10 mg/mL of the active ingredient. In another preferred embodiment, the formulation contains 2 mg/mL to 5 mg/mL of the active ingredient.

The formulation typically has a pH of about 2.0 to about 5.0, a pH of about 2.5 to about 4.5, a pH of about 2.5 to about 4.0, a pH of about 3.0 to about 3.5 or a pH of about 3.0 to about 3.6. In some embodiments, the formulation has a pH of about 2, a pH of about 2.5, a pH of about 3.0, a pH or about 3.3, a pH of about 3.5 or a pH of about 4.0. In some embodiments, the formulation has a pH of 2.0 to 5.0, a pH of 2.5 to 4.5, a pH of about 2.5 to about 4.0, a pH of 3.0 to 3.5 or a pH of 3.0 to 3.6.

As described more fully in the examples, the stability of AMG 416 depends on the pH of the solution. The present inventors have found that the two major degradants are the result of C-terminal deamidation and homodimer formation. In addition, the present inventors have found that the time course of degradation by these pathways is a function of pH. See Example 6. At low pH, degradation by C-terminal deamidation predominates (see FIG. 10) while at higher pH, degradation by homodimer formation predominates (see FIG. 11). Thus, formation of the two major degradants have the opposite relationship between pH and extent of degradation. These opposing trends underlie the overall stability data over the range of pH values and support the identification of about pH 3.0 to 3.5 as the pH of maximum stability of AMG 416 solutions.

Typically, the formulation contains a physiologically acceptable buffering agent that maintains the pH of the formulation in the desired range. In one embodiment, the buffer maintains a pH of about 2.0 to about 5.0, a pH of about 2.5 to about 4.5, a pH of about 2.5 to about 4.0, a pH of about 3.0 to about 3.5 or a pH of about 3.0 to about 3.6.

In some embodiments, the buffer maintains a pH of about 2, a pH of about 2.5, a pH of about 3.0, a pH of about 3.3, a pH of about 3.5 or a pH of about 4.0. In some embodiments, the buffer maintains a pH of 2.0 to 5.0, a pH of 2.5 to 4.5, a pH of 2.5 to about 4.0, a pH of 3.0 to 3.5 or a pH of 3.0 to 3.6.

Any buffer that is capable of maintaining the pH of the formulation at any pH or within any pH range provided above is suitable for use in the formulations of the present disclosure, provided that it does not react with other components of the formulation, cause visible precipitates to form, or otherwise cause the active ingredient to become chemically destabilized. The buffer used in the present formulation typically comprises a component selected from the group consisting of succinate, citrate, malate, edentate, histidine, acetate, adipate, aconitate, ascorbate, benzoate, carbonate, bicarbonate, maleate, glutamate, lactate, phosphate, and tartarate, or a mixture of these buffers. In a preferred embodiment, the buffer comprises succinate, e.g., sodium succinate.

The concentration of the buffer is selected so that pH stabilization as well as sufficient buffering capacity is provided. In one embodiment, the buffer is present in the formulation at a concentration of from about 0.5 to about 100 mmol/L, from about 0.75 to about 50 mmol/L, from about 1 to about 20 mmol/L, or from about 10 to about 20 mmol/L. In other embodiments, the buffer is present at about 5 mmol/L, at about 10 mmol/L, at about 15 mmol/L or about 20 mmol/L. In other embodiments, the buffer is present in the formulation at a concentration of from 0.5 to 100 mmol/L, from 0.75 to 50 mmol/L, from 1 to 20 mmol/L, or from 10 to 20 mmol/L. In a preferred embodiment, the buffer is present at about 10 mmol/L. In another preferred embodiment, the buffer is succinate present at about 10 mmol/L.

From the point of view of compatibility of the liquid formulation with intravenous administration, it would be desirable for the pH of the liquid formation to be as near as possible to the physiological pH. Liquid formulations that have a pH that is far from physiological pH or that are strongly buffered can cause pain or discomfort when administration. As has been discussed, liquid formulations of AMG 416 at physiological pH or higher would not remain stable over an extended period of time. Therefore, in a preferred embodiment, the liquid formulation of the present disclosure is weakly buffered so that the quantity injected is quickly neutralized by physiological fluids of the body of the subject. It is surprising that good stability and good control of pH is maintained with the low buffer concentration. In a preferred embodiment, the HCl salt of AMG 416 is used in the preparation of the liquid formulation to minimize buffer capacity. Because HCl is a strong acid, it does not act as a buffer. This provides an advantage over the use of a weaker acid, such as an acetic acid. Using the acetate salt of AMG 416, for example, would itself provide some buffering capacity and allow less flexibility to set the buffering capacity of the formulation and may result in a formulation which is more resistant to neutralization within the body and therefore less well tolerated. Because AMG 416 is a polycationic peptide, the effect would be enhanced compared to most peptides which have a more neutral character.

It is generally desirable for a formulation to be administered by intravenous or other parenteral route to be isotonic with bodily fluids. In some embodiments, the formulation of the present disclosure contains a physiologically acceptable tonicity modifier. Tonicity modifiers useful in the present disclosure may include sodium chloride, mannitol, sucrose, dextrose, sorbitol, potassium chloride, or mixtures thereof. In a preferred embodiment, the tonificier is sodium chloride.

When a tonicity agent is present, it is preferably present in an amount sufficient to make the liquid formulation approximately isotonic with bodily fluids (i.e., about 270 to about 300 mOsm/L) and suitable for parenteral injection into a mammal, such as a human subject, into dermal, subcutaneous, or intramuscular tissues or IV. Isotonicity can be measured by, for example, using a vapor pressure or ice-freezing type osmometer. Depending upon the concentrations of the other components in the formulation, sodium chloride is present in the formulation at a concentration of about 7.0 to about 10 mg/mL, about 7.5 to about 9.5 mg/mL, or about 8.0 to about 9.0 mg/mL. In a one embodiment, sodium chloride is present in the formulation at a concentration of about 8.5 mg/mL. In other embodiments, sodium chloride is present in the formulation at a concentration of 7.0 to 10 mg/mL, 7.5 to 9.5 mg/mL, or 8.0 to 9.0 mg/mL.

The formulations of the present disclosure may include other conventional pharmaceutical carriers, excipients or adjuvants. For example, the formulations of the present invention may include stabilizing agents (e.g., EDTA and/or sodium thiosulfate) or preservatives (e.g., benzyl alcohol). In addition, the formulations of the present disclosure may including additional medicinal and/or pharmaceutical agents. For example, in methods of treating treat SHPT in hemodialysis patients with CKD-MBD, AMG 416 can be coadministered with one or more active agents in renal osteodystrophy, such as a vitamin D therapy (e.g., paricalcitol) which is an established treatment for SHPT.

In one embodiment, the formulation has less than 5% degradation when stored at about 2-8° C. for 1 year. In another embodiment, the formulation has less than 5% degradation when stored at room temperature for 1 year. In another embodiment, the formulation has less than 10% degradation when stored at about 2-8° C. for 1 year. In another embodiment, the formulation has less than 10% degradation when stored at room temperature for 1 year. In another embodiment, the formulation has less than 5% degradation when stored at about 2-8° C. for 2 years. In another embodiment, the formulation has less than 5% degradation when stored at room temperature for 2 years. In another embodiment, the formulation has less than 10% degradation when stored at about 2-8° C. for 2 years. In another embodiment, the formulation has less than 10% degradation when stored at room temperature for 2 years.

In one embodiment, the liquid formulation comprises 0.1 mg/mL to 20 mg/mL of the therapeutic peptide, a buffer that maintains the formulation at a pH of 2.0 to 5.0, and a sufficient concentration of sodium chloride for the formulation to be approximately isotonic is provided. In another embodiment, the liquid formulation comprises 1 mg/mL to 15 mg/mL of the therapeutic peptide, a buffer that maintains the formulation at a pH of 2.5 to 4.5, and a sufficient concentration of sodium chloride for the formulation to be approximately isotonic is provided. In another embodiment, the liquid formulation comprises 2.5 mg/mL to 10 mg/mL of the therapeutic peptide, a buffer that maintains the formulation at a pH of 2.5 to 4.0, and a sufficient concentration of sodium chloride for the formulation to be approximately isotonic is provided. In another embodiment, the liquid formulation comprises 2.5 mg/mL to 5 mg/mL of the therapeutic peptide, a buffer that maintains the formulation at a pH of 2.5 to 3.5, and a sufficient concentration of sodium chloride for the formulation to be approximately isotonic is provided. In another embodiment, the formulation comprises 2 mg/mL to 20 mg/mL of the therapeutic peptide in aqueous solution, a succinate buffer that maintains the formulation at a pH of about 3.0 to 3.5, and a sufficient concentration of sodium chloride for the formulation to be approximately isotonic is provided.

In one embodiment, the liquid formulation comprises 0.1 mg/mL to 20 mg/mL of AMG 416, a buffer that maintains the formulation at a pH of 2.0 to 5.0, and a sufficient concentration of sodium chloride for the formulation to be approximately isotonic is provided. In another embodiment, the liquid formulation comprises 1 mg/mL to 15 mg/mL of AMG 416, a buffer that maintains the formulation at a pH of 2.5 to 4.5, and a sufficient concentration of sodium chloride for the formulation to be approximately isotonic is provided. In another embodiment, the liquid formulation comprises 2.5 mg/mL to 10 mg/mL of AMG 416, a buffer that maintains the formulation at a pH of 2.5 to 4.0, and a sufficient concentration of sodium chloride for the formulation to be approximately isotonic is provided. In another embodiment, the liquid formulation comprises 2.5 mg/mL to 5 mg/mL of AMG 416, a buffer that maintains the formulation at a pH of 2.5 to 3.5, and a sufficient concentration of sodium chloride for the formulation to be approximately isotonic is provided. In another embodiment, the formulation comprises 2 mg/mL to 20 mg/mL of AMG 416 in aqueous solution, a succinate buffer that maintains the formulation at a pH of about 3.0 to 3.5, and a sufficient concentration of sodium chloride for the formulation to be approximately isotonic is provided.

In a preferred embodiment, the formulations of the present disclosure are prepared by placing an amount of buffer calculated to generate the desired pH into a suitable vessel and dissolving it with water for injection (WFI), adding an amount of material (e.g., the hydrochloride salt of AMG 416) sufficient to achieve the desired concentration of the active ingredient (e.g., AMG 416), adding an amount of tonicity modifier (or mixture of tonicity modifiers) calculated to render the resulting formulation isotonic with body fluids, and adding the amount of WFI necessary to bring the total volume to the desired concentration. After the ingredients are mixed, the pH is adjusted to about 3.0 to about 3.5, and the components are again mixed.

If an adjustment is required in order to achieve the desired pH range, the pH value may be adjusted by means of suitable solutions; with acidic solutions if a reduction of the pH value is indicated and with alkaline solution if an increase of pH value is indicated. Non-limiting examples of suitable acidic solutions are, e.g., hydrochloric acid, phosphoric acid, citric acid and sodium or potassium hydrogen phosphate. Non-limiting examples of suitable alkaline solutions are alkali and alkali earth hydroxides, alkali carbonates, alkali acetates, alkali citrates and dialkali hydrogen phosphates, e.g., sodium hydroxide, sodium acetate, sodium carbonate, sodium citrate, disodium or dipotassium hydrogen phosphate, or ammonia.

The procedure is typically carried out at a temperature from about 2-8° C. to about 50° C., and at atmospheric pressure. The resulting formulation may then be transferred to unit dosage or multi-dosage containers (such as bottles, vials, ampoules or prefilled syringes) for storage prior to use.

The formulations can be prepared and administered as described above. Alternatively, the formulations can be administered after dissolving, dispersing, etc. the formulation (prepared as described above) in a carrier, such as, for example, an infusion fluid or in the blood/fluid returned to the patient during hemodialysis (e.g., during rinse-back).

The preparation of liquid formulations according to the present disclosure are known, or will be apparent, to those skilled in the art, for example, see Remington's Pharmaceutical Sciences, Mack Publishing Company, Easton, PA, 17th edition, 1985.

EXAMPLES

The following examples, including the experiments conducted and the results achieved, are provided for illustrative purposes only and are not to be construed as limiting the scope of the appended claims.

Example 1

Solubility of AMG 416 in Succinate Buffered Saline

In this study, the solubility of AMG 416 in succinate buffered-saline was investigated. AMG 416 HCl (103 mg powder, 80 mg peptide) was dissolved in 200 µL of sodium succinate buffered saline (25 mM succinate, 0.9% saline, pH 4.5). After briefly vortexing, a clear solution was obtained with a nominal concentration of 400 mg/mL. Because expansion of the solution volume was not determined, the solubility of AMG 416 can be conservatively stated as at least 200 mg/mL. Although the maximal solubility was not determined in this experiment, AMG 416 is soluble in pH 4.5 succinate buffered saline to concentrations of at least 200 mg/mL.

Example 2

Concentration Dependent Stability Study

In this study, the stability of AMG 416 over a range of concentrations in succinate-buffered saline (pH 4.5) was investigated. The solution of 200 mg/mL AMG 416 from Example 1, supra, was diluted further with 200 µL of succinate-buffered saline (pH 4.5) to a nominal concentration of 200 mg/mL, which was serially diluted with succinate-buffered saline (pH 4.5) to 66, 20, 6.7, 2.2 and 0.67 mg/mL. The samples were kept at room temperature (i.e., about 25° C.) and aliquots were analyzed by HPLC at intervals up to 29 days. A second series of AMG 416 samples covering the concentration range 20 to 0.67 mg/mL were incubated at 40° C. and analyzed in the same manner.

The purity at the 29-day time point for samples at room temperature and 40° C. is provided in Tables 1 and 2, respectively. The results provide a stability profile of AMG 416 as a function of concentration and temperature.

TABLE 1

RT Stability of AMG 416 in 25 mM succinate-buffered saline (pH 4.5)

| Concentration | Purity at Time (Days) | | | | | |
|---|---|---|---|---|---|---|
| (mg/ml) | 0 | 1 | 2 | 5 | 13 | 29 |
| 200 | 99.8 | 99.6 | 98.4 | 96.4 | 89.0 | 63.8 |
| 66 | 99.6 | 99.4 | 99.0 | 98.1 | 97.7 | 91.5 |
| 20 | 99.6 | 99.7 | 99.7 | 99.6 | 99.3 | 98.7 |
| 6.7 | 99.4 | 99.6 | 99.5 | 99.5 | 99.3 | 98.9 |
| 2.2 | 99.3 | 99.2 | 99.3 | 99.4 | 99.3 | 99.1 |
| 0.67 | 99.4 | 99.5 | 99.5 | 99.7 | 99.5 | 99.3 |

TABLE 2

40° C. Stability of AMG 416 in 25 mM succinate-buffered saline (pH 4.5)

| Concentration | Purity at Time (Days) | | | | | |
|---|---|---|---|---|---|---|
| (mg/ml) | 0 | 1 | 2 | 5 | 13 | 29 |
| 20 | 99.6 | 99.1 | 98.1 | n.d. | 90.5 | 72.9 |
| 6.7 | 99.4 | 99.1 | 98.7 | n.d. | 95.2 | 90.0 |
| 2.2 | 99.3 | 99.3 | 99.0 | 98.4 | 97.0 | 94.3 |
| 0.67 | 99.4 | 99.4 | 99.3 | 99.0 | 97.2 | 94.4 |

Figure 1B:
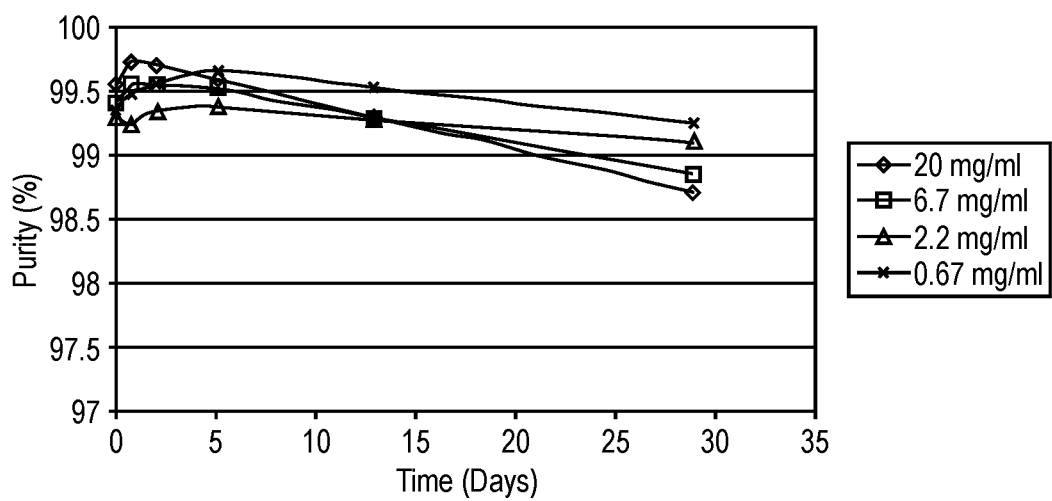
Figure 2:
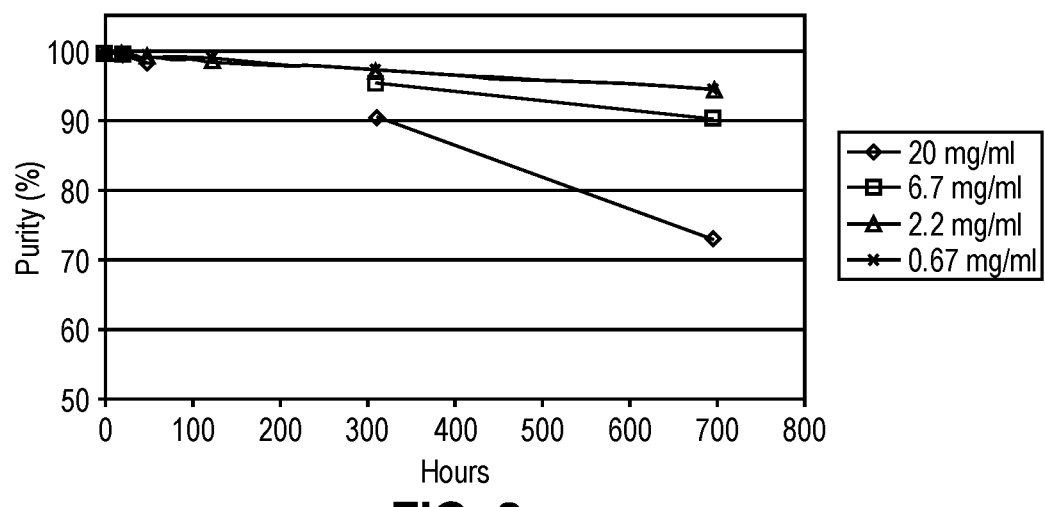
FIG. 2 is a graph plotting purity (%) as a function of time (days) for AMG 416 solutions in succinate-buffered saline (pH 4.5) at 40° C. having concentrations in the range of 20, 6.7, 2.2 and 0.67 mg/mL of AMG 416.

The time course of AMG 416 degradation as a function of concentration at room temperature is shown in FIG. 1A. In FIG. 1B, the scale is expanded to more clearly illustrate the degradation pattern at drug concentrations of 20 mg/mL and below. The time course of AMG 416 degradation as a function of concentration at 40° C. is shown in FIG. 2. The data show that AMG 416 solution stability is related to concentration in the study range from 0.67 mg/mL to 200 mg/mL. The data also shows that AMG 416 solution stability is related to temperature of incubation.

Table 3 shows predictions of extent of degradation for solutions of various concentrations of AMG 416 at room temperature, based on extent of degradation at 29 days, room temperature storage in pH 4.5 SBS. The room temperature 29-day data from Table 1 was extrapolated to the stated time period by assuming linear degradation kinetics. Room temperature data was extrapolated to 5° C. A 20° C. difference was assumed, equivalent to a 4-fold lower rate of degradation. Extrapolations were carried out using a simple application of the Arrhenius equation, where at 10° C. rise in temperature provides a 2-fold increase in reaction rate, assuming the same reaction mechanism and that activation energy for each relevant reaction is around 50 kJ/mol.

Bolded values indicate concentration/storage conditions which have less than 10% degradation, which may be preferable for a liquid formulation.

TABLE 3

Stability Predictions for Velcalcetide Solutions

| Concentration | Predicted extent of degradation at: | | | |
|---|---|---|---|---|
| (mg/mL) | 2 yr RT | 1 yr RT | 2 yr 5° C. | 1 yr 5° C. |
| 66 | >100 | >100 | 50.1 | 25.0 |
| 20 | 20.9 | 10.4 | 5.2 | 2.6 |
| 6.7 | 13.9 | 7.0 | 3.5 | 1.7 |
| 2.2 | 5.2 | 2.6 | 1.3 | 0.7 |
| 0.67 | 2.7 | 1.4 | 0.7 | 0.3 |

Comparison of the data shown in Tables 1 and 2 allows assessment of temperature increase as a tool to predict the long-term stability of AMG 416 solutions. The data from 0.67 to 20 mg/mL is presented in Table 4, infra, and shows acceleration of degradation at 40° C., which is markedly higher than that predicted by Arrhenius (with the assumptions described, supra). This suggests that accelerated stability data will predict a greater extent of degradation than will be observed at the actual storage temperature.

TABLE 4

Temperature and Concentration Dependence of
AMG 416 Degradation in pH 4.5 Solution

| Concentration (mg/mL) | Degradation at 29 days, RT (%) | Degradation at 29 days, 40 C (%) | Acceleration RT -> 40 C. (fold) | Predicted acceleration (fold) |
|---|---|---|---|---|
| 20 | 0.9 | 26.7 | 29.7 | 4 |
| 6.7 | 0.5 | 9.4 | 18.8 | 4 |
| 2.2 | 0.2 | 5.0 | 25.0 | 4 |
| 0.67 | 0.1 | 5.0 | 50.0 | 4 |

Example 3

Stability of Liquid Formulations of AMG 416 Over Range of pH

In this study, the stability of liquid formulations of AMG 416, at a concentration of 10 mg/mL, was determined over a range of pH in succinate-buffered saline. AMG 416 HCl (257 mg powder) was dissolved in 20 ml of pH 4.5 succinate buffered saline to provide 10.0 mg/ml peptide concentration (adjusted for peptide content of powder). The solution was divided evenly into five 4 mL portions which were adjusted to pH 2, 3, 4, 5 and 6, respectively, with NaOH and HCl as needed. Three 1 mL solutions were aliquoted from each portion and incubated at 2-8° C., room temperature (about 25° C.), and 40° C., respectively. The remaining 1 mL solution in each aliquot was diluted with pH 4.5 succinate buffered saline to 4 mL of 2.5 mg/mL peptide concentration, pH adjusted, and incubated in the same manner. Samples were retrieved according to schedule and diluted with deionized water to 1.0 mg/mL for HPLC analysis.

The purity at the 28 day time point for all samples tested is provided in Table 5 (note: the starting purity value was 99.3% for this study). The results provide a stability profile as a function of pH, temperature and concentration.

TABLE 5

Purity at 28-Day Time Point for AMG 416 Solutions.

| | 10 mg/mL | | | 2.5 mg/mL | | |
|---|---|---|---|---|---|---|
| | 2-8° C. | RT | 40° C. | 2-8° C. | RT | 40° C. |
| pH 2 | 99.1 | 98.7 | 94.0 | 98.9 | 98.7 | 89.8 |
| pH 3 | 99.4 | 99.1 | 98.2 | 99.1 | 99.0 | 97.2 |
| pH 4 | 99.4 | 98.6 | 85.0 | 99.2 | 98.9 | 92.2 |
| pH 5 | 99.0 | 93.8 | 64.4 | 98.9 | 96.1 | 73.0 |
| pH 6 | 96.9 | 71.8 | 53.6 | 97.0 | 80.0 | 52.9 |

Figure 3A:
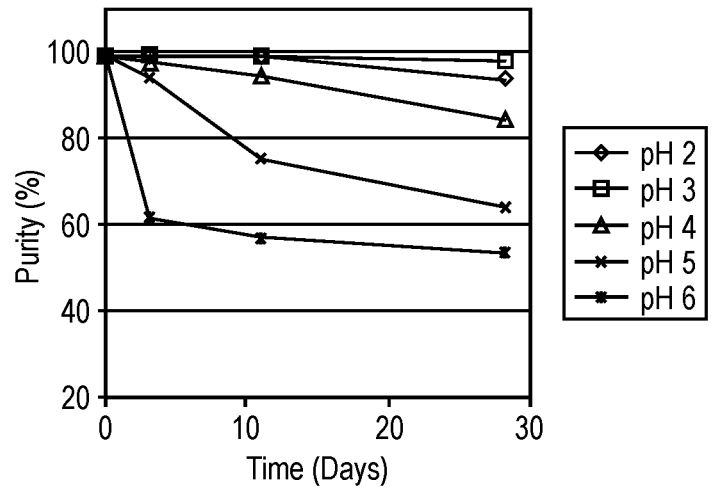
FIGS. 3A-3B are graphs plotting purity (%) as a function of time (days) for AMG 416 solutions in succinate-buffered saline (pH 2, 3, 4, 5 and 6) at 40° C.
Figure 3B:
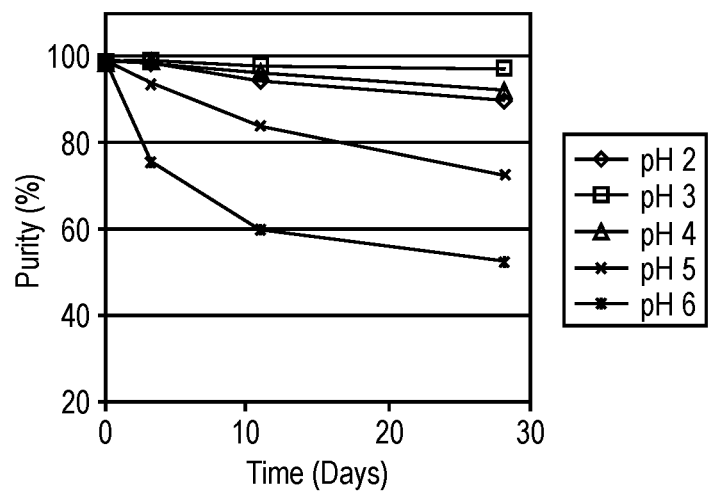

The time course of AMG 416 degradation as a function of pH is shown in FIG. 3. In both the 10 mg/mL (FIG. 3A) and the 2.5 mg/mL (FIG. 3B) solutions, the least degradation is observed at pH 3. In both solutions, degradation at pH 6 proceeds most rapidly with purity approaching 50% by the 29 day point. HPLC analysis showed that the major degradant at pH 2 different than that observed at pH greater than 3. At lower pH, the degradation is predominantly by deamidation by hydrolysis and at higher pH, the degradation is predominantly formation of the homodimer.

Figure 4A:
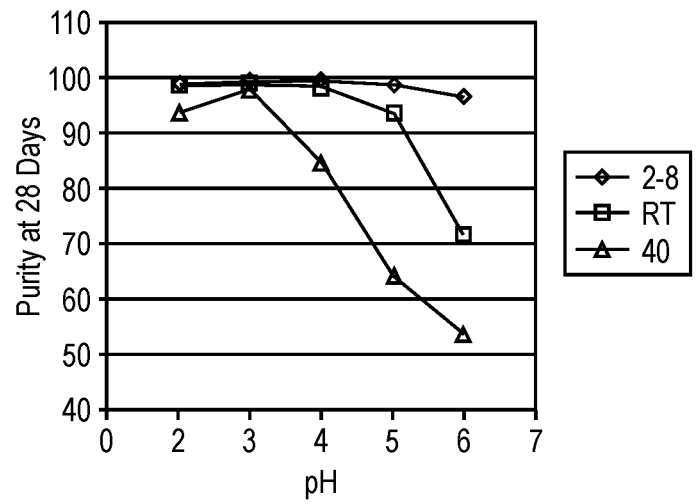
FIGS. 4A-4B are graphs plotting purity (%) at 28 days as a function of pH for AMG 416 solutions in succinate-buffered saline at 2-8° C., RT and 40° C.
Figure 4B:
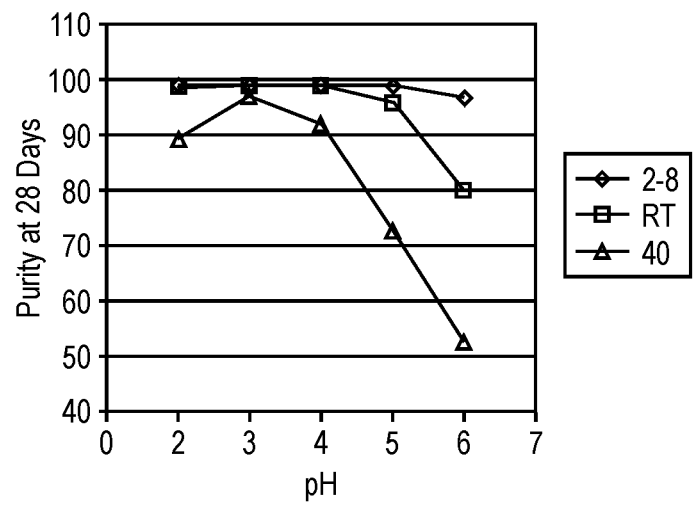

The stability profile as a function of pH at the 28 day point is shown in FIG. 4. It can be seen again in both the 10 mg/mL (FIG. 4A) and 2.5 mg/mL (FIG. 4B) that in this set of experiments, the pH of least degradation is approximately 3.0. In addition, the decreases in purity are related to the temperature at all pH levels, with the least degradation observed in the samples incubated at 2-8° C., and the most degradation observed in the samples incubated at 40° C.

Based on the extent of degradation at 28 days, predictions of the extent of degradation were calculated as described, supra. The predictions for the 10 mg/mL solution are provided in Table 6 and the predictions for the 2.5 mg/mL are provided in Table 7. Bolded values indicate conditions which show less than 10% degradation, and which may be preferred for a liquid formulation. Conditions where the sample at 28 days show slightly higher purity than the initial data are presented as 0.0% for all projections.

These extrapolations suggest less than 10% degradation after 2 years at room temperature for 2.5 or 10 mg/mL solutions at pH 3. In general, higher temperature data predicts greater degradation at 2 years than the lower temperature data. Thus, for the 10 mg/mL studies (Table 6), while pH 3 is predicted to be less than 10% degradation from all temperature data, the 2-8° C. data predicts a lower extent of degradation than the higher temperatures, and in fact at 2-8° C., the pH 4 data is also supportive of less than 10% degradation. Similarly, at 2.5 mg/mL, a pH range from 2-4 is predicted to have less than 10% degradation over 2 years at RT when extrapolated from the 2-8° C. data.

TABLE 6

Stability Predictions for AMG 416 10 mg/mL Solutions
Based on Extent of Degradation at 28 days.

| | Observed degradation at 28 days (%) | Calculated Degradation | | | |
|---|---|---|---|---|---|
| | | at 360 d (%) | at 1 y RT (%) | at 2 y 5° C. (%) | at 2 y RT (%) |
| 2-8° C. | | | | | |
| pH = 2 | 0.3 | 3.8 | 15.4 | 7.7 | 30.7 |
| pH = 3 | −0.2 | 0.0 | 0.0 | 0.0 | 0.0 |
| pH = 4 | −0.1 | 0.0 | 0.0 | 0.0 | 0.0 |
| pH = 5 | 0.3 | 3.5 | 13.8 | 6.9 | 27.6 |
| pH = 6 | 1.9 | 23.9 | 95.7 | 47.8 | >100 |
| RT | | | | | |
| pH = 2 | 0.6 | 8.1 | 8.1 | 4.0 | 16.1 |
| pH = 3 | 0.2 | 2.6 | 2.6 | 1.3 | 5.1 |
| pH = 4 | 0.7 | 8.6 | 8.6 | 4.3 | 17.1 |
| pH = 5 | 5.6 | 71.4 | 71.4 | 35.7 | >100 |
| pH = 6 | 26.9 | >100 | >100 | >100 | >100 |
| 40° C. | | | | | |
| pH = 2 | 5.3 | 68.4 | 17.1 | 8.6 | 34.2 |
| pH = 3 | 1.1 | 14.1 | 3.5 | 1.8 | 7.0 |
| pH = 4 | 14.3 | >100 | 45.8 | 22.9 | 91.7 |
| pH = 5 | 34.9 | >100 | >100 | 55.9 | >100 |
| pH = 6 | 45.1 | >100 | >100 | 72.2 | >100 |

TABLE 7

Stability Predictions for AMG 416 2.5 mg/mL Solutions
Based on Extent of Degradation at 28 days.

| | Observed degradation at 28 days (%) | Calculated Degradation (%) | | | |
|---|---|---|---|---|---|
| 2-8° C. | | 1 y 2-8° C. | 1 y RT | 2 y 2-8° C. | 2 y RT |
| pH = 2 | 0.0 | 0.0 | 0.0 | 0.0 | 0.0 |
| pH = 3 | 0.0 | 0.0 | 0.0 | 0.0 | 0.0 |

TABLE 7-continued

Stability Predictions for AMG 416 2.5 mg/mL Solutions
Based on Extent of Degradation at 28 days.

| | | | | | |
|---|---|---|---|---|---|
| pH = 4 | −0.1 | 0.0 | 0.0 | 0.0 | 0.0 |
| pH = 5 | 0.2 | 2.9 | 11.8 | 5.9 | 23.5 |
| pH = 6 | 0.8 | 10.7 | 43.0 | 21.5 | 86.0 |

| | Observed degradation | Calculated Degradation (%) | | | |
|---|---|---|---|---|---|
| RT | at 28 days (%) | 1 y | 1 y RT | 2 y 2-8° C. | 2 y RT |
| pH = 2 | 0.6 | 7.9 | 7.9 | 4.0 | 15.9 |
| pH = 3 | 0.0 | 0.0 | 0.0 | 0.0 | 0.0 |
| pH = 4 | 0.3 | 3.6 | 3.6 | 1.8 | 7.2 |
| pH = 5 | 2.9 | 37.7 | 37.7 | 18.9 | 75.5 |
| pH = 6 | 18.1 | 231.0 | 231.0 | 115.5 | 462.1 |

| | Observed degradation | Calculated Degradation (%) | | | |
|---|---|---|---|---|---|
| 40° C. | at 28 days (%) | 1 y | 1 y RT | 2 y 2-8° C. | 2 y RT |
| pH = 2 | 9.1 | 116.5 | 29.1 | 14.6 | 58.3 |
| pH = 3 | 1.8 | 22.5 | 5.6 | 2.8 | 11.3 |
| pH = 4 | 6.9 | 88.7 | 22.2 | 11.1 | 44.3 |
| pH = 5 | 26.1 | 333.6 | 83.4 | 41.7 | 166.8 |
| pH = 6 | 45.0 | 575.7 | 143.9 | 72.0 | 287.8 |

Table 8 presents the temperature acceleration effect for these data in a similar way to Table 4, supra. This again indicates that temperature elevation tends to provide greater acceleration of degradation than is expected by extrapolation based on simple application of Arrhenius principles.

TABLE 8

Temperature acceleration as a function of pH.

| | 28 d Deg 10 mg/mL | | | Acceleration: 10 mg/mL data | | | | |
|---|---|---|---|---|---|---|---|---|
| | 2-8° C. | RT | 40° C. | RT/2-8 | predicted | 40 C./2-8 | predicted | 40 C./RT | predicted |
| pH 2 | 0.2 | 0.6 | 5.3 | 3 | 4 | 28 | 16 | 9 | 4 |
| pH 3 | −0.1 | 0.2 | 1.1 | >2 | 4 | >10 | 16 | 6 | 4 |
| pH 4 | −0.1 | 0.7 | 14.3 | >7 | 4 | >100 | 16 | 22 | 4 |
| pH 5 | 0.3 | 5.6 | 34.9 | 19 | 4 | 116 | 16 | 6 | 4 |
| pH 6 | 2.4 | 27.5 | 45.7 | 12 | 4 | 19 | 16 | 2 | 4 |

At each pH value, the degradation data for each of three temperatures is compared to data from the other two temperatures to calculate the observed acceleration. The predicted acceleration is by simple application of Arrhenius principles as described above. As described, infra, HPLC analysis shows that the predominant degradation mechanism at pH less than about 3 is different than that observed at pH greater than about 3.

Example 4

Effect of Tonicifying Excipients on Stability

In this study, the effects of various pharmaceutical excipients on the stability of AMG 416 in liquid formulation were determined. A 10 mg/mL solution of AMG 416 and stock solutions of mannitol, glycine, arginine, NaCl and $Na_2SO_4$ at 2× isotonic concentrations were prepared. The pH of the AMG 416 solution and the five excipient solutions and deionized water separately were adjusted to pH 3.5 using HCl/NaOH. 500 μL aliquots of each of the six solutions were added to glass vials and 500 μL of the AMG 416 solution was added to the same vials and mixed well. This was performed in triplicate to provided eighteen sample vials, each containing 5 mg/mL AMG 416 and an isotonic concentration of the excipient (or deionized water). This was repeated with a set of solutions adjusted to pH 4.5, providing a further eighteen sample vials. The samples were incubated and removed for HPLC analysis at relevant time points.

The stability data at the 56-day time point is shown in Table 9. A range of stability behavior was observed as a function of excipient. Under most conditions tested, NaCl formulations showed the least amount of degradation. The exceptions are for the 2-8° C. data at pH 3.5 and 4.5. More variability was observed for other excipients, although arginine appeared to be deleterious in the 40° C. samples and in the pH 4.5 sample at room temperature (about 25° C.), and sodium sulfate appeared to be deleterious in the pH 4.5 samples at room temperature and at 40° C.

TABLE 9

Extent of degradation (%) at 56 days for 5 mg/mL AMG 416 Solution

| Temp | 2-8° C. | | RT | | 40° C. | |
|---|---|---|---|---|---|---|
| pH | 3.5 | 4.5 | 3.5 | 4.5 | 3.5 | 4.5 |
| DI Water | 0.0 | 0.7 | 1.0 | 3.6 | 8.2 | 24 |
| Mannitol | 0.0 | 0.5 | 0.5 | 2.2 | 4.9 | 23 |

TABLE 9-continued

Extent of degradation (%) at 56 days for 5 mg/mL AMG 416 Solution

| Temp | 2-8° C. | | RT | | 40° C. | |
|---|---|---|---|---|---|---|
| pH | 3.5 | 4.5 | 3.5 | 4.5 | 3.5 | 4.5 |
| Gly | 0.0 | 0.6 | 0.6 | 6.4 | 17 | 28 |
| Arg | 0.0 | 0.5 | 0.6 | 29 | 28 | 67 |
| NaCl | 0.1 | 1.1 | 0.3 | 1.8 | 3.0 | 18 |
| $Na_2SO_4$ | 0.0 | 0.4 | 0.4 | 51 | 9.4 | 30 |

Table 10 extrapolates the data to 2 years at room temperature storage, and a similar trend is seen as discussed, supra, in that higher temperature storage generally predicts more rapid degradation than is expected by simple application of Arrhenius principles.

TABLE 10

Predicted extent of degradation (%) for 5 mg/mL AMG 416 Solutions After 2 Year Storage at Room Temperature.

| Temp | 2-8° C. | | RT | | 40° C. | |
|---|---|---|---|---|---|---|
| pH | 3.5 | 4.5 | 3.5 | 4.5 | 3.5 | 4.5 |
| DI Water | 1 | 35 | 13 | 47 | 27 | 77 |
| Mannitol | 0 | 28 | 7 | 28 | 16 | 75 |
| Gly | 3 | 31 | 8 | 83 | 55 | 90 |
| Arg | 2 | 27 | 7 | >100 | 90 | >100 |
| NaCl | 4 | 56 | 4 | 24 | 10 | 58 |
| Na$_2$SO$_4$ | 2 | 22 | 5 | >100 | 31 | 98 |

The data shows that sodium chloride may be a suitable tonicity modifier for AMG 416 solution formulations.

Example 5

Solution Stability in Different Buffers

In this study, the stability of liquid formulations of AMG 416 was evaluated in four different buffers over 9 days. Buffered saline solutions were prepared at 25 mM concentration, pH 4.5, for four different anionic buffers in the sodium salt form: acetate, citrate, lactate and succinate. AMG 416 HCl (powder) was dissolved in each buffered solution to provide a 2.5 mg/mL solution and the pH was adjusted to 4.5 with HCl/NaOH. The solutions were diluted further with pH 4.5 buffer to 1.0 mg/mL and 0.25 mg/mL. Each of the resulting solutions was split to two glass HPLC vials, one stored at 2-8° C. and one at room temperature (about 25° C.). HPLC analysis was conducted at 0, 4 and 9 days for determination of potency and purity.

The purity of AMG 416 in most samples at all time points was 100%, with the exception of a few small peaks for the citrate sample at 9 days which may be attributed to baseline variation. In all buffers tested, AMG 416 showed good stability during the 9 day study.

Example 6

Stability in Buffered Solutions at pH 2.25, 2.5 3.0 and 3.5

In this study, the stability of a liquid formulation of AMG 416 under low pH conditions was investigated. Succinate-buffered saline (10 mM, pH 3.5) was prepared by dissolving 59 mg of succinic acid in 45 ml of lab processed (deionized) water and adjusting the pH to 3.5 using 1N HCl and 1N NaOH as needed, and q.s. to 50 ml. In the same way, a 10 mM, pH 3.5 sodium lactate (56 mg/50 mL) buffer solution was prepared.

AMG 416 HCl (128 mg powder) was dissolved in 20 mL of succinate buffer to provide a 5 mg/mL AMG 416 solution which was split into two equal 10 mL portions. NaCl (90 mg) was added to one portion and mannitol (500 mg) was added to the other. Each 10 mL portion was split again into two equal 5 mL portions and the pH was adjusted to 2.25 and 3.5, respectively, with 1N HCl and 1N NaOH. In the same way, four 5 mL solutions were prepared using lactate buffer. 1.0 mL of each of the (eight) resulting solutions was added to 3 serum sample vials. In addition, the remaining pH 2.25, succinate-buffered AMG 416 solution containing NaCl was adjusted to pH 2.5 and 0.5 mL aliquots were added to 3 serum sample vials and the remaining pH 3.5 succinate buffered solution with NaCl was adjusted to pH 3.0 and 0.5 mL aliquots were added to 3 serum sample vials. See Table 11.

At each time point (0, 2, 8, 12 and 24 weeks) all 30 samples were retrieved from storage, equilibrated to room temperature (about 25° C.), and a 100 µL aliquot was diluted to 0.5 mg/mL with water for RP-HPLC analysis. The remaining samples were resealed and returned to their respective storage conditions.

TABLE 11

Description of Sample Numbers

| pH | 2.25 | | | | 3.5 | | | | 2.5 | 3.0 |
|---|---|---|---|---|---|---|---|---|---|---|
| Buffer | Lactate | | Succinate | | Lactate | | Succinate | | Succinate | |
| Excipient | NaCl | Mann | NaCl | Mann | NaCl | Mann | NaCl | Mann | NaCl | NaCl |
| 2-8° C. | 1 | 2 | 3 | 4 | 5 | 6 | 7 | 8 | 25 | 28 |
| RT | 9 | 10 | 11 | 12 | 13 | 14 | 15 | 16 | 26 | 29 |
| 40° C. | 17 | 18 | 19 | 20 | 21 | 22 | 23 | 24 | 27 | 30 |

Representative HPLC data for the study are shown in FIGS. 5 and 6. The HPLC trace shown in FIG. 5 is a pH 2.25 sample stored for 67 days at 40° C. (5 mg/mL, 87.8% purity). FIG. 5B shows a different scale to see at the impurities. FIG. 6 illustrates the effect of increasing pH to 3.5 for the otherwise equivalent formulation (pH 3.5, 40° C., 5 mg/mL, 67 days, 91.7% purity). FIG. 6B shows a different scale to see the impurities. As in the prior study, a notable difference is seen in the degradant profile as pH changes.

AMG 416 purity as a function of time is presented in Table 12 (10 mM buffer concentration: L=lactate; S=succinate. tonicity modifier: N=0.9% NaCl; M=5% mannitol). Note that the lot used contained 3.4% dimer at time 0. The 14 day time point for sample 26 was omitted due to an error in sample preparation.

Figure 7:
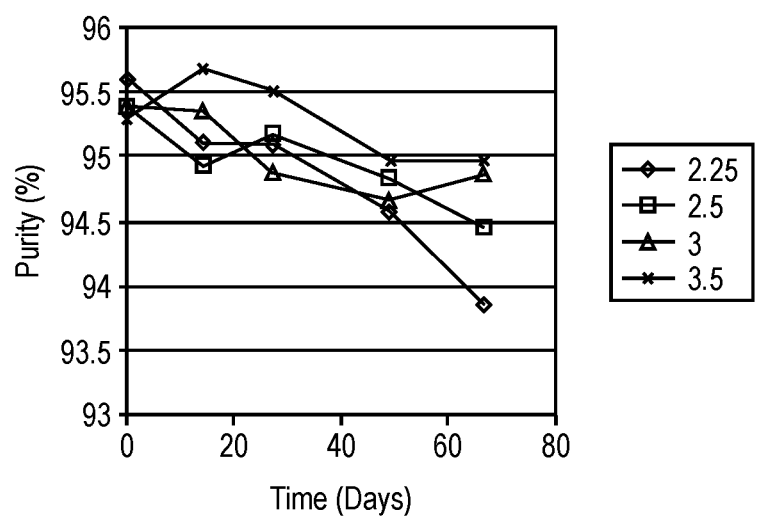
FIG. 7 is a graph plotting purity (%) as a function of time (days) for a series of AMG 416 solutions (5 mg/mL) in succinate-buffered saline (pH 2.25, 2.5, 3.0 and 3.5) at 2-8° C.
Figure 8:
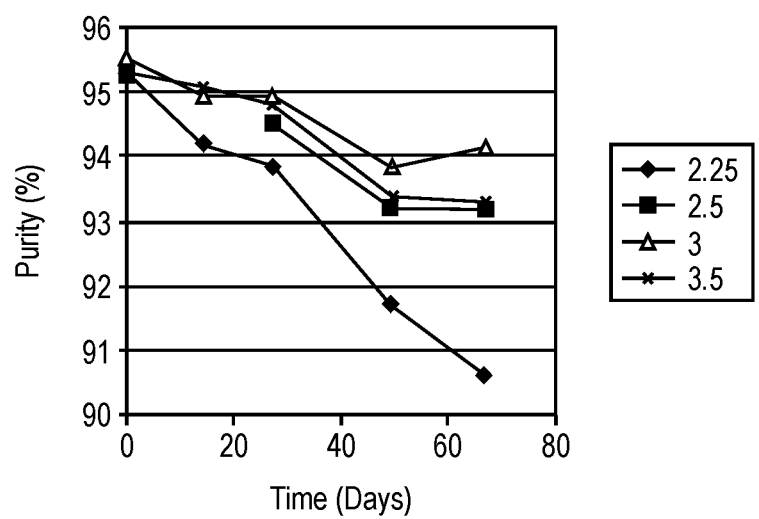
FIG. 8 is a graph plotting purity (%) as a function of time (days) for a series of AMG 416 solutions (5 mg/mL) in succinate-buffered saline (pH 2.25, 2.5, 3.0 and 3.5) at RT.
Figure 9:
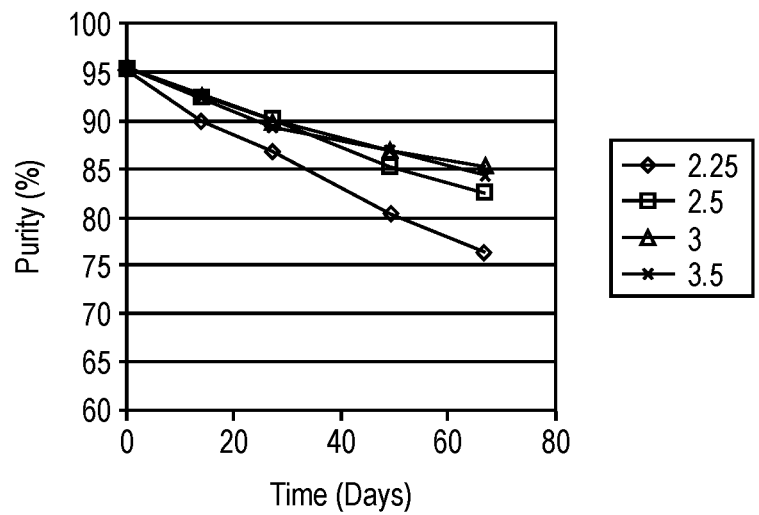
FIG. 9 is a graph plotting purity (%) as a function of time (days) for a series of AMG 416 solutions (5 mg/mL) in succinate-buffered saline (pH 2.25, 2.5, 3.0 and 3.5) at 40° C.

Selected data trends are represented in graphical form in FIGS. 7-9.

TABLE 12

Stability of AMG 416 Solution at 5 mg/mL to 67 days in Buffered Solution

| | | | | | Purity (%) at Time (Days) | | | | |
|---|---|---|---|---|---|---|---|---|---|
| Sample | pH | Temp | Buffer | Tonic. | 0 | 14 | 27 | 49 | 67 |
| 1 | 2.25 | 5 | L | N | 96.8 | 96.4 | 97.0 | 95.7 | 95.7 |
| 2 | 2.25 | 5 | L | M | 96.8 | 96.4 | 95.9 | 96.0 | 95.7 |
| 3 | 2.25 | 5 | S | N | 95.6 | 95.1 | 95.1 | 94.6 | 93.8 |
| 4 | 2.25 | 5 | S | M | 95.4 | 95.1 | 95.4 | 94.0 | 94.0 |
| 5 | 3.5 | 5 | L | N | 96.9 | 96.6 | 96.4 | 95.8 | 96.2 |
| 6 | 3.5 | 5 | L | M | 96.8 | 96.9 | 96.9 | 96.0 | 94.5 |
| 7 | 3.5 | 5 | S | N | 95.3 | 95.7 | 95.5 | 95.0 | 95.0 |
| 8 | 3.5 | 5 | S | M | 95.4 | 95.2 | 95.1 | 95.1 | 94.4 |
| 9 | 2.25 | 25 | L | N | 96.9 | 96.4 | 95.2 | 94.0 | 92.8 |
| 10 | 2.25 | 25 | L | M | 96.9 | 96.6 | 95.6 | 93.2 | 94.9 |
| 11 | 2.25 | 25 | S | N | 95.3 | 94.2 | 93.9 | 91.7 | 90.6 |
| 12 | 2.25 | 25 | S | M | 95.6 | 94.5 | 94.1 | 92.5 | 92.1 |
| 13 | 3.5 | 25 | L | N | 96.6 | 96.3 | 96.3 | 94.7 | 95.2 |
| 14 | 3.5 | 25 | L | M | 96.5 | 96.2 | 95.3 | 94.8 | 93.3 |
| 15 | 3.5 | 25 | S | N | 95.3 | 95.1 | 94.8 | 93.4 | 93.3 |
| 16 | 3.5 | 25 | S | M | 95.8 | 95.3 | 94.7 | 93.5 | 93.6 |
| 17 | 2.25 | 40 | L | N | 96.7 | 91.9 | 87.8 | 83.5 | 79.4 |
| 18 | 2.25 | 40 | L | M | 96.5 | 93.8 | 89.5 | 86.6 | 83.0 |
| 19 | 2.25 | 40 | S | N | 95.3 | 89.9 | 86.9 | 80.4 | 76.3 |
| 20 | 2.25 | 40 | S | M | 95.4 | 91.8 | 89.6 | 85.3 | 82.9 |
| 21 | 3.5 | 40 | L | N | 96.7 | 94.3 | 91.7 | 89.5 | 86.2 |
| 22 | 3.5 | 40 | L | M | 96.6 | 92.2 | 85.9 | 79.5 | 77.3 |
| 23 | 3.5 | 40 | S | N | 95.3 | 92.3 | 89.3 | 86.8 | 84.2 |
| 24 | 3.5 | 40 | S | M | 95.6 | 91.6 | 88.5 | 84.2 | 80.3 |
| 25 | 2.5 | 5 | S | N | 95.4 | 94.9 | 95.2 | 94.8 | 94.4 |
| 26 | 2.5 | 25 | S | N | 95.2 | ND | 94.5 | 93.2 | 93.2 |
| 27 | 2.5 | 40 | S | N | 95.3 | 92.3 | 90.3 | 85.0 | 82.4 |
| 28 | 3.0 | 5 | S | N | 95.4 | 95.4 | 94.9 | 94.7 | 94.9 |
| 29 | 3.0 | 25 | S | N | 95.6 | 94.9 | 95.0 | 93.9 | 94.2 |
| 30 | 3.0 | 40 | S | N | 95.3 | 92.5 | 90.0 | 86.9 | 85.2 |

FIG. 7 provides solution stability of AMG 416 (5 mg/mL) in succinate-buffered saline as a function of pH under refrigerated conditions (2-8° C.). FIG. 8 provides solution stability of AMG 416 (5 mg/mL) in succinate-buffered saline as a function of pH after storage at room temperature. FIG. 9, provide solution stability of AMG 416 (5 mg/mL) in succinate-buffered saline as a function of pH after storage at 40° C.

Figure 10A:
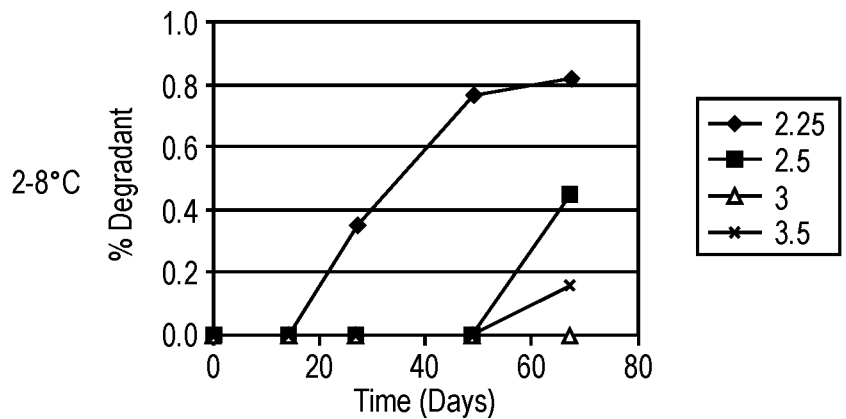
FIGS. 10A-10C are graphs plotting degradant (%) as a function of time (days) for a series of AMG 416 solutions (5 mg/mL) in succinate-buffered saline (pH 2.25, 2.5, 3.0 and 3.5). The time-course of C-terminal deamidation is shown at 2-8° C.
Figure 10B:
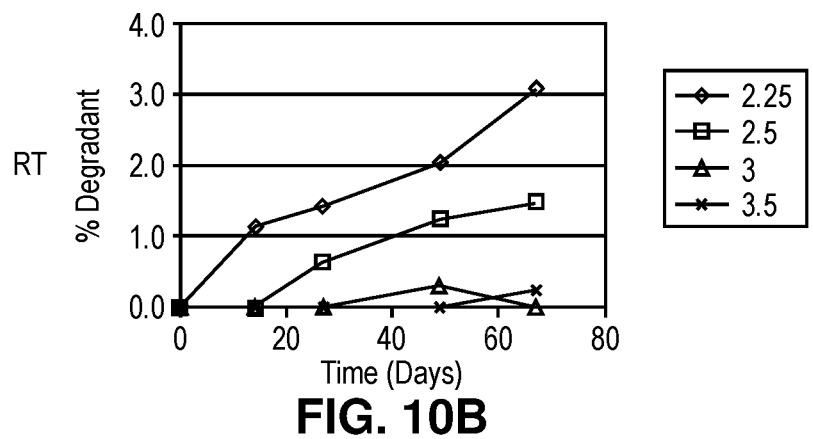
Figure 10C:
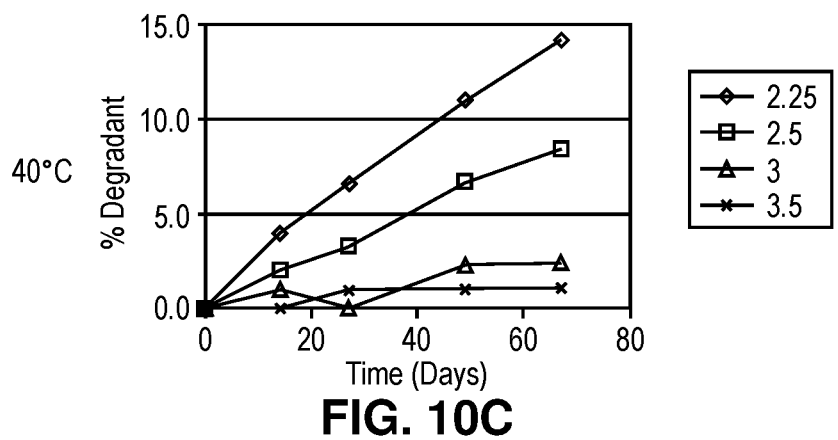
Figure 11A:
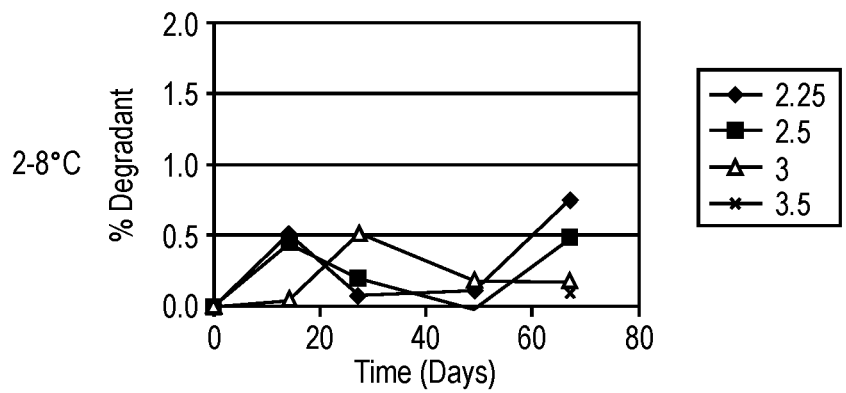
FIGS. 11A-11C are graphs plotting degradant (%) as a function of time (days) for a series of AMG 416 solutions (5 mg/mL) in succinate-buffered saline ((pH 2.25, 2.5, 3.0 and 3.5). The time-course of homodimer formation is shown at 2-8° C.
Figure 11B:
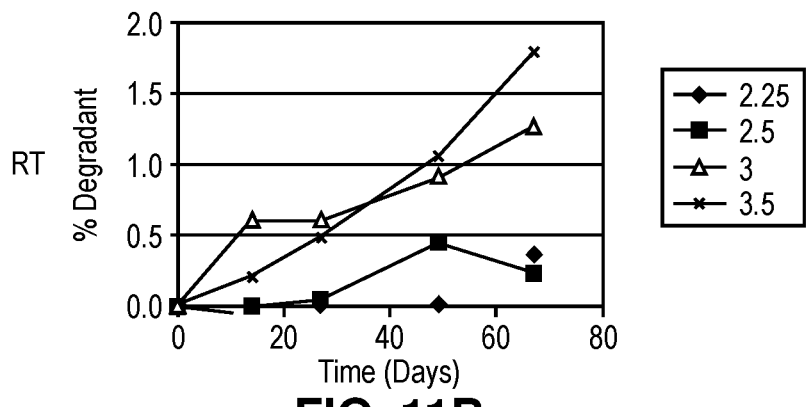
Figure 11C:
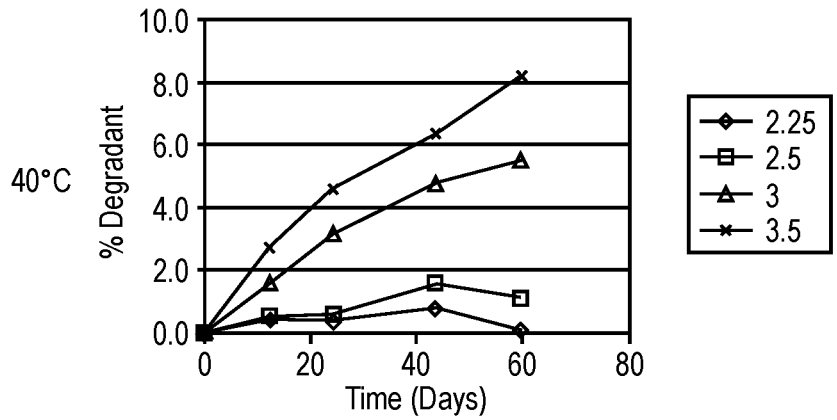

The degradant profile at the latest time point is presented in Table 13, and the time course of appearance of the two major degradants (C-terminal deamidation and homodimer formation) is shown in Tables 14 and 15. FIGS. 10 and 11 present the time course of degradation to these individual products (C-terminal deamidation and homodimer formation, respectively) as a function of pH for selected formulations (those formulations for which a complete set of pH conditions are available, i.e., those containing NaCl and succinate, but not lactate or mannitol).

FIG. 10 indicates a clear pH dependency for deamidation, with significantly greater degradation by this pathway at pH 2.25 than at higher pH, and a direct correspondence between pH and amount of deamidation. In contrast, homodimer formation presented in FIG. 11 shows the opposite relationship between pH and extent of degradation. These opposing trends underlie the overall stability data presented in FIGS. 7-9, and Maximal stability for AMG 416 solutions in this set of experiments was observed at pH of 3.0±0.5.

The correlation between stability and excipient composition is less clear. Regarding the buffer selection (succinate vs. lactate), inspection of the data in Tables 12-14 shows no clear pattern of preference for either buffer with respect to any of the major degradants at pH 2.25 or 3.5. All samples with succinate buffer showed lower purity at time 0 than the corresponding lactate-buffered samples, due to the larger integration of the homodimer peak. The reason for this is unclear, but may indicate a change in the relative absorbance for the parent and dimer as a function of buffer. However, as noted above, subsequent incubation provides essentially identical rate of degradation in the presence of either buffer. Regarding the choice of tonicity modifier (NaCl or mannitol), sodium chloride appears to enhance the rate of deamidation at pH 2.25 (see Table 13, samples 9-12 at 25° C. and especially samples 17-20 at 40° C.). However, NaCl appears to suppress (compared to mannitol) the degradation to the homodimer at pH 3.5 (Table 14, samples 13-16 at 25° C. and especially samples 21-24 at 40° C.).

TABLE 13

Degradant Profile for AMG 416 (5 mg/mL) Solution after 67 Days

| | | | | Major Impurities (% total area) | | | | |
|---|---|---|---|---|---|---|---|---|
| t = 67 Days | | | | Acid | Dimer | Dimer Trisulfide | Deacetyl | Trisulfide |
| pH | Temp | Buffer | Tonic. | 8.1 mins | 9.3 mins | 9.5 | 7.4 mins | 8.2 mins |
| 2.25 | 5 | L | N | 0.8 | 0.4 | | | |
| 2.25 | 5 | L | M | 0.5 | 0.6 | | | |

TABLE 13-continued

Degradant Profile for AMG 416 (5 mg/mL) Solution after 67 Days

| | | | | Major Impurities (% total area) | | | | |
|---|---|---|---|---|---|---|---|---|
| t = 67 Days | | | | Acid | Dimer | Dimer Trisulfide | Deacetyl | Trisulfide |
| pH | Temp | Buffer | Tonic. | 8.1 mins | 9.3 mins | 9.5 | 7.4 mins | 8.2 mins |
| 2.25 | 5 | S | N | 0.8 | 0.8 | | | |
| 2.25 | 5 | S | M | 1.1 | 0.1 | | | |
| 3.5 | 5 | L | N | | 0.1 | | | |
| 3.5 | 5 | L | M | 1.2 | 1.6 | | | |
| 3.5 | 5 | S | N | 0.2 | 0.1 | | | |
| 3.5 | 5 | S | M | 0.7 | −0.1 | | | |
| 2.25 | 25 | L | N | 2.5 | 0.3 | | 0.3 | 0.9 |
| 2.25 | 25 | L | M | 1.2 | 0.4 | | 0.3 | |
| 2.25 | 25 | S | N | 3.1 | 0.4 | | 0.4 | |
| 2.25 | 25 | S | M | 1.6 | 0.9 | | | |
| 3.5 | 25 | L | N | | 1.4 | | | |
| 3.5 | 25 | L | M | | 3.1 | | | |
| 3.5 | 25 | S | N | 0.2 | 1.8 | | | |
| 3.5 | 25 | S | M | | 2.1 | | 0.1 | |
| 2.25 | 40 | L | N | 13.9 | 0.4 | 0.7 | 2.9 | |
| 2.25 | 40 | L | M | 8.7 | 1.6 | 0.6 | 2.0 | 0.3 |
| 2.25 | 40 | S | N | 14.2 | 0.0 | 0.2 | 3.1 | |
| 2.25 | 40 | S | M | 8.9 | 2.4 | 0.6 | 2.5 | 0.3 |
| 3.5 | 40 | L | N | 1.4 | 7.4 | 1.0 | | 0.7 |
| 3.5 | 40 | L | M | 0.5 | 17.0 | 0.5 | | 1.0 |
| 3.5 | 40 | S | N | 1.0 | 8.1 | 0.6 | 0.1 | 0.6 |
| 3.5 | 40 | S | M | 1.0 | 11.7 | 0.7 | | 1.3 |
| 2.5 | 5 | S | N | 0.5 | 0.5 | | | |
| 2.5 | 25 | S | N | 1.5 | 0.2 | | 0.4 | |
| 2.5 | 40 | S | N | 8.4 | 1.1 | 0.4 | 1.9 | |
| 3.0 | 5 | S | N | | 0.2 | | 0.4 | |
| 3.0 | 25 | S | N | | 1.3 | | 0.1 | |
| 3.0 | 40 | S | N | 2.4 | 5.5 | 0.6 | 0.6 | 0.5 |

10 mM buffer concentration:
L = Lactate;
S = succinate.
Tonicity modifier:
N = 0.9% NaCl;
M = 5% mannitol).
Value for dimer % reflects increase in degradant after subtracting starting value.

10 mM buffer concentration: L=Lactate; S=succinate. Tonicity modifier: N=0.9% NaCl; M=5% mannitol). Value for dimer % reflects increase in degradant after subtracting starting value.

TABLE 14

Deamidation in AMG 416 (5 mg/mL) Solution at Time Points up to 67 Days

| | | | | | % Degradant at Time (Days) | | | | |
|---|---|---|---|---|---|---|---|---|---|
| Sample | pH | Temp | Buffer | Tonic. | 0 | 14 | 27 | 49 | 67 |
| 1 | 2.25 | 5 | L | N | 0.1 | | | 0.7 | 0.8 |
| 2 | 2.25 | 5 | L | M | | | 0.9 | 0.8 | 0.5 |
| 3 | 2.25 | 5 | S | N | | | 0.4 | 0.8 | 0.8 |
| 4 | 2.25 | 5 | S | M | | | | 0.3 | 1.1 |
| 5 | 3.5 | 5 | L | N | | | 0.3 | 0.4 | |
| 6 | 3.5 | 5 | L | M | | | | | 1.2 |
| 7 | 3.5 | 5 | S | N | | | | | 0.2 |
| 8 | 3.5 | 5 | S | M | | | | | 0.7 |
| 9 | 2.25 | 25 | L | N | | | 1.3 | 1.6 | 2.5 |
| 10 | 2.25 | 25 | L | M | | | 1.2 | 1.2 | 1.2 |
| 11 | 2.25 | 25 | S | N | | 1.1 | 1.4 | 2.0 | 3.1 |
| 12 | 2.25 | 25 | S | M | | 0.7 | 1.0 | 1.3 | 1.6 |
| 13 | 3.5 | 25 | L | N | | | | | |
| 14 | 3.5 | 25 | L | M | | | | | |
| 15 | 3.5 | 25 | S | N | | | | | 0.2 |
| 16 | 3.5 | 25 | S | M | | | | | |
| 17 | 2.25 | 40 | L | N | | 3.4 | 6.6 | 10.2 | 13.9 |
| 18 | 2.25 | 40 | L | M | | 2.5 | 4.8 | 7.0 | 8.7 |
| 19 | 2.25 | 40 | S | N | | 3.9 | 6.6 | 11.0 | 14.2 |

TABLE 14-continued

Deamidation in AMG 416 (5 mg/mL) Solution at Time Points up to 67 Days

| Sample | pH | Temp | Buffer | Tonic. | % Degradant at Time (Days) | | | | |
|---|---|---|---|---|---|---|---|---|---|
| | | | | | 0 | 14 | 27 | 49 | 67 |
| 20 | 2.25 | 40 | S | M | | 2.3 | 4.2 | 6.4 | 8.9 |
| 21 | 3.5 | 40 | L | N | | | 0.9 | 0.9 | 1.4 |
| 22 | 3.5 | 40 | L | M | | | 0.5 | 0.6 | 0.5 |
| 23 | 3.5 | 40 | S | N | | | 1.0 | 1.0 | 1.0 |
| 24 | 3.5 | 40 | S | M | | | 0.4 | 0.3 | 1.0 |
| 25 | 2.5 | 5 | S | N | | | | | 0.5 |
| 26 | 2.5 | 25 | S | N | | | 0.7 | 1.3 | 1.5 |
| 27 | 2.5 | 40 | S | N | | 2.0 | 3.3 | 6.7 | 8.4 |
| 28 | 3.0 | 5 | S | N | | | | | |
| 29 | 3.0 | 25 | S | N | | | | 0.3 | |
| 30 | 3.0 | 40 | S | N | | 1.0 | | 2.2 | 2.4 |

10 mM buffer concentration:
L = Lactate;
S = succinate.
Tonicity modifier:
N = 0.9% NaCl;
M = 5% mannitol).

10 mM buffer concentration: L=Lactate; S=succinate. Tonicity modifier: N=0.9% NaCl; M=5% mannitol).

Maximal stability for AMG 416 solutions in this set of experiments was observed at pH of 3.0±0.5. The rate of total degradation at pH 2.5 and 3.5 is similar, but the degradant profile is different. Stability at pH 2.25 is inferior due to the greater quantities of deamidation observed. While some effect of excipient can be observed on the stability profile, the data does not indicate an overall preference among the excipient systems studied, when formulated at pH 3.0.

TABLE 15

AMG 416 Degradation to Homodimer in 5 mg/mL Solution at Time Points up to 67 Days

| Sample | pH | Temp | Buffer | Tonic. | Dimer (% Increase) | | | | |
|---|---|---|---|---|---|---|---|---|---|
| | | | | | 0 | 14 | 27 | 49 | 67 |
| 1 | 2.25 | 5 | L | N | 0.0 | 0.5 | −0.1 | 0.5 | 0.4 |
| 2 | 2.25 | 5 | L | M | 0.0 | 0.4 | 0.0 | 0.0 | 0.6 |
| 3 | 2.25 | 5 | S | N | 0.0 | 0.5 | 0.1 | 0.1 | 0.8 |
| 4 | 2.25 | 5 | S | M | 0.0 | 0.3 | 0.0 | 0.2 | 0.1 |
| 5 | 3.5 | 5 | L | N | 0.0 | 0.2 | 0.1 | 0.2 | 0.1 |
| 6 | 3.5 | 5 | L | M | 0.0 | −0.1 | 0.0 | 0.2 | 1.6 |
| 7 | 3.5 | 5 | S | N | 0.0 | −0.4 | −0.2 | 0.0 | 0.1 |
| 8 | 3.5 | 5 | S | M | 0.0 | 0.2 | 0.1 | −0.1 | −0.1 |
| 9 | 2.25 | 25 | L | N | 0.0 | 0.5 | 0.4 | 0.5 | 0.3 |
| 10 | 2.25 | 25 | L | M | 0.0 | 0.3 | 0.1 | 0.5 | 0.4 |
| 11 | 2.25 | 25 | S | N | 0.0 | −0.1 | 0.0 | 0.0 | 0.4 |
| 12 | 2.25 | 25 | S | M | 0.0 | 0.5 | 0.5 | 0.2 | 0.9 |
| 13 | 3.5 | 25 | L | N | 0.0 | 0.3 | 0.3 | 0.9 | 1.4 |
| 14 | 3.5 | 25 | L | M | 0.0 | 0.4 | 0.3 | 1.5 | 3.1 |
| 15 | 3.5 | 25 | S | N | 0.0 | 0.2 | 0.5 | 1.1 | 1.8 |
| 16 | 3.5 | 25 | S | M | 0.0 | 0.5 | 1.0 | 1.4 | 2.1 |
| 17 | 2.25 | 40 | L | N | 0.0 | 0.6 | 0.8 | 0.5 | 0.4 |
| 18 | 2.25 | 40 | L | M | 0.0 | 0.0 | 0.3 | 0.6 | 1.6 |
| 19 | 2.25 | 40 | S | N | 0.0 | 0.5 | 0.4 | 0.8 | 0.0 |
| 20 | 2.25 | 40 | S | M | 0.0 | 0.6 | 0.6 | 1.3 | 2.4 |
| 21 | 3.5 | 40 | L | N | 0.0 | 2.4 | 3.7 | 5.5 | 7.4 |
| 22 | 3.5 | 40 | L | M | 0.0 | 4.1 | 9.5 | 15.0 | 17.0 |
| 23 | 3.5 | 40 | S | N | 0.0 | 2.8 | 4.6 | 6.3 | 8.1 |
| 24 | 3.5 | 40 | S | M | 0.0 | 3.7 | 6.6 | 9.0 | 11.7 |
| 25 | 2.5 | 5 | S | N | 0.0 | 0.4 | 0.2 | 0.0 | 0.5 |
| 26 | 2.5 | 25 | S | N | 0.0 | | 0.1 | 0.5 | 0.2 |
| 27 | 2.5 | 40 | S | N | 0.0 | 0.6 | 0.6 | 1.5 | 1.1 |
| 28 | 3.0 | 5 | S | N | 0.0 | 0.0 | 0.5 | 0.2 | 0.2 |

TABLE 15-continued

AMG 416 Degradation to Homodimer in 5 mg/mL Solution at Time Points up to 67 Days

| | | | | | Dimer (% Increase) | | | | |
|---|---|---|---|---|---|---|---|---|---|
| Sample | pH | Temp | Buffer | Tonic. | 0 | 14 | 27 | 49 | 67 |
| 29 | 3.0 | 25 | S | N | 0.0 | 0.6 | 0.6 | 0.9 | 1.3 |
| 30 | 3.0 | 40 | S | N | 0.0 | 1.6 | 3.2 | 4.8 | 5.5 |

10 mM buffer concentration:
L = Lactate;
S = succinate.
Tonicity modifier:
N = 0.9% NaCl;
M = 5% mannitol).
Note
that degradation is expressed as an increase in dimer content (not total dimer) as the API used for the experiment contained appreciable quantity of dimer.

(10 mM buffer concentration: L=Lactate; S=succinate. Tonicity modifier: N=0.9% NaCl; M=5% mannitol). Note that degradation is expressed as an increase in dimer content (not total dimer) as the API used for the experiment contained appreciable quantity of dimer.

Maximal stability for AMG 416 solutions in this set of experiments was observed at pH of 3.0±0.5. Analysis of solutions formulated at pH 2.5 or 3.5 show different degradation profiles, with C-terminal amide hydrolysis being the largest degradant at low pH whereas homodimer formation was larger at higher pH. Liquid formulations at pH 3.0 have predicted total degradation of 2-4% over 2 years under refrigerated conditions.

Example 7

Robustness Study

In this study, the stability of a liquid formulation of AMG 416 under a variety of manufacturing and analytical conditions was investigated. Fourteen formulation testing groups were prepared, each having a different combination of pH (2.7, 3.3 or 3.9), peptide concentration (4, 5 or 6 mg/mL) and salt concentration (0.7, 0.85 or 1.0%). The osmolality of each formulation was kept the same (succinate 10 mM). See Table 16.

TABLE 16

Formulation Testing Groups

| Sample | pH | Succinate (mM) | Peptide (mg/mL) | NaCl (%) |
|---|---|---|---|---|
| 1 | 3.3 | 10 | 5 | 0.85 |
| 2 | 3.9 | 10 | 4 | 1.0 |
| 3 | 2.7 | 10 | 4 | 0.85 |
| 4 | 3.9 | 10 | 6 | 0.7 |
| 5 | 3.3 | 10 | 4 | 0.7 |
| 6 | 3.9 | 10 | 6 | 1.0 |
| 7 | 3.3 | 10 | 5 | 1.0 |
| 8 | 3.3 | 10 | 5 | 0.85 |
| 9 | 3.9 | 10 | 5 | 0.85 |
| 10 | 3.3 | 10 | 6 | 0.85 |
| 11 | 2.7 | 10 | 6 | 0.85 |
| 12 | 2.7 | 10 | 5 | 1.0 |
| 13 | 2.7 | 10 | 5 | 0.7 |
| 14 | 3.9 | 10 | 4 | 0.7 |

Samples (2.1 mL) of each of the formulation testing groups were dispensed into 3 mL Type 1B glass vials (Schott, Germany) and sealed (rubber stopper). Sets of the vials were stored upright for three months at temperatures of 4° C., 25° C. or 40° C. Changes in the pH, osmolality, percent AMG 416, and degradants were assessed over three months.

The time-dependent response surface defined by the three factors (pH, % peptide and % NaCl) was estimated by fitting a statistical model that describes such surface to the data for each HPLC response and at each temperature (JMP® statistical discovery software, SAS). Monte Carlo simulation was used to generate the distributions of the predicted HPLC responses at the set point (pH=3.3, peptide=5% and NaCl=8.5%) as a function of the random variation of factors around the set point and the random noise.

No significant change in pH and osmolality with time were noted. At 4° C. and 25° C., purity remained 92% or greater, deamidation was 4% or less and homodimer formation was 4% or less over the entire length of the study. At 40° C., purity, deamidation and homodimer formation was seen beginning at 1 month. However, deamidation and homodimer formation were decreased as the pH range narrowed around 3.3, indicating that pH has a significant impact on the formation of these degradants.

Figure 12A:
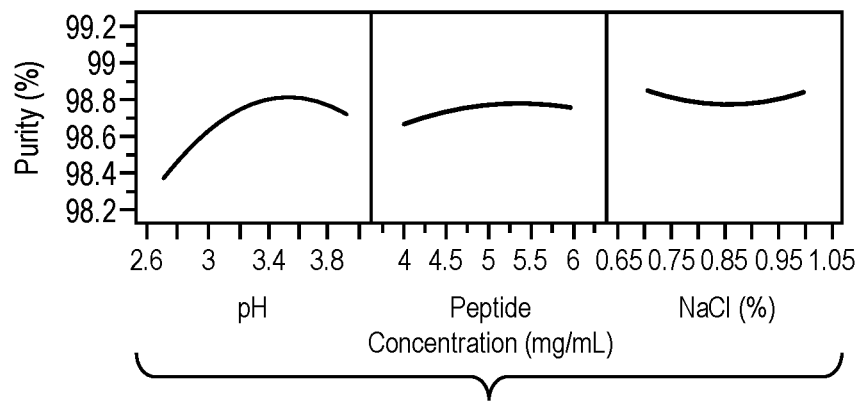
FIGS. 12A-12C are graphs plotting purity (%) as a function of pH (2.8-3.8), AMG 416 concentration (4-6 mg/mL) and NaCl (0.7-1.0%) for a series of solutions in succinate-buffered saline stored at 2-8° C.
Figure 12B:
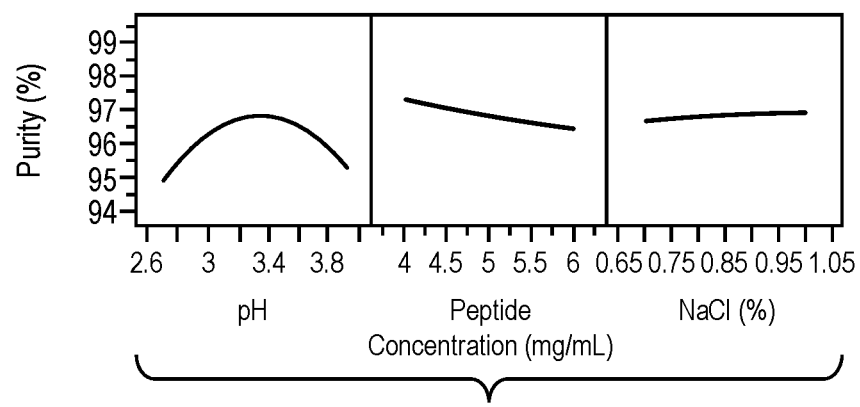
Figure 12C:
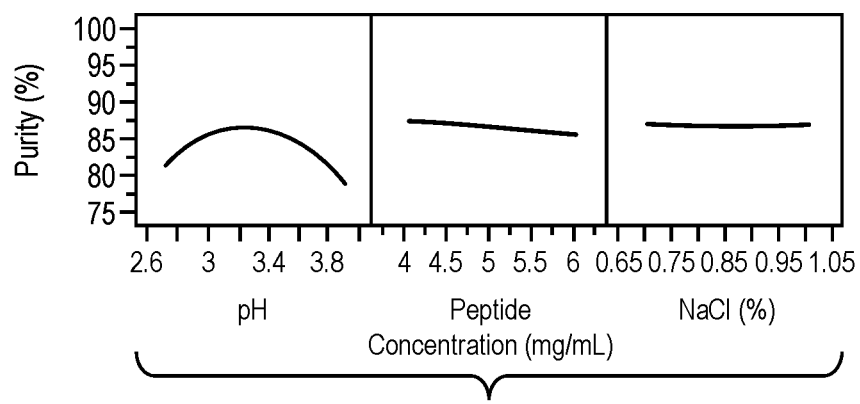

Based on this data, it is possible to provide a prediction of the purity profile over a range of pH from 2.8 to 3.8. As shown in FIG. 12, the purity at each temperature is strongly dependent on pH, and less dependent on peptide concentration and NaCl within the range tested. Under refrigerated conditions, the effect of pH is less significant at values above pH 3.3, but at room temperature (about 25° C.), higher pH values are associated with more rapid degradation. Formulations for therapeutic use may be subject to long term storage under refrigerated conditions. In addition, consideration should also be given to potential exposure of the formulation to higher temperatures during manufacturing, packaging, labeling and clinical use. Thus, in this set of experiments, it was observed that a pH value in the tested range of 2.8 to 3.8 (3.3±0.5) would be suitable for AMG 416 formulations.

Example 8

Long Term Stability of Liquid Formulations of AMG 416 Over Range of pH

In this study, the long term stability of a liquid formulation of AMG 416, at a concentration of 3.4 mg/mL, was determined over a range of pH in succinate-buffered saline. USP purified water (1200 mL) was dispensed into a glass beaker. Sodium succinate (4.05 g) and sodium chloride (13.5 g) were added and stirred to dissolve. The pH was adjusted to 2.5 with 1N NaOH and/or 1N HCl as required. AMG 416 HCl (5.5 g powder weight) was added, stirred to dissolve, and q.s. to 1500 mL with purified water to provide 3.4 mg/mL solution (AMG 416). The solution was divided into three portions and the pH for each portion was adjusted to 2.5, 3.0 and 3.5, respectively. Each solution was filtered separately through 0.22 micron PVDF filter and dispense 2 mL to 5-cc vials. After being stoppered, sealed, and labeled, the vials were place in designated stability chambers at 5° C.±3, 25° C.±2, and 40° C.±2. Samples were retrieved according to schedule and diluted with deionized water to 1.0 mg/mL for HPLC analysis. The purity at months 0, 1, 2, 3, 5, 12 and 24 is provided in Table 17 (note: the starting purity value was 99.2% for this study). The results provide a long term stability profile of a 3.4 mg/mL liquid formulation of AMG 416 as a function of pH and temperature.

TABLE 17

Purity at Time Point up to 24 Months for AMG 416 Solutions.

| pH | Temp (° C.) | Purity (%) at Time (Months) | | | | | | | Degradation at 2 y |
|---|---|---|---|---|---|---|---|---|---|
| | | 0 | 1 | 2 | 3 | 5 | 12 | 24 | |
| 2.5 | 5 | 99.2 | 99.0 | 98.8 | 98.8 | 98.1 | 96.8 | 94.8 | 4.4 |
| | 25 | 99.2 | 96.9 | 95.2 | 93.4 | 89.3 | 80.9 | 68.5 | 30.7 |
| | 40 | 99.2 | 88.8 | 81.9 | 75.3 | 60.9 | 39.1 | 20.4 | 78.8 |
| 3 | 5 | 99.2 | 99.1 | 99.1 | 99.2 | 98.7 | 98.3 | 97.7 | 1.5 |
| | 25 | 99.2 | 98.2 | 97.5 | 96.7 | 95.0 | 91.1 | 84.6 | 14.6 |
| | 40 | 99.2 | 93.7 | 90.2 | 86.4 | 78.9 | 61.6 | 39.2 | 60.0 |
| 3.5 | 5 | 99.2 | 99.2 | 99.2 | 99.2 | 98.8 | 98.6 | 98.3 | 0.9 |
| | 25 | 99.2 | 98.6 | 98.1 | 97.6 | 96.2 | 93.4 | 89.2 | 10.0 |
| | 40 | 99.2 | 94.6 | 91.5 | 88.7 | 83.1 | 67.5 | 46.1 | 53.1 |

Figure 13A:
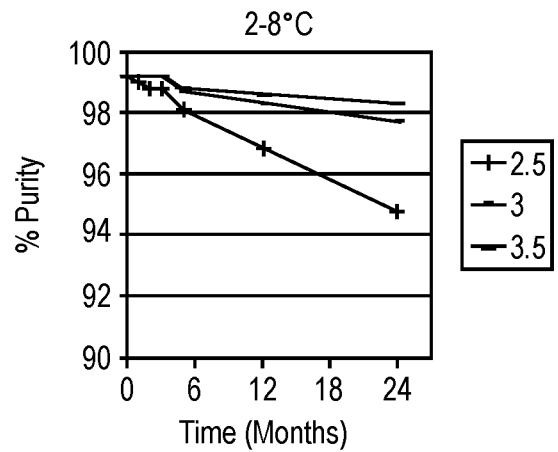
FIGS. 13A-13C are graphs plotting purity (%) as a function of time (months) for a series of AMG 416 solutions (3.4 mg/mL) in succinate-buffered saline (pH 2.5, 3.0, 3.5) stored at 2-8° C.
Figure 13B:
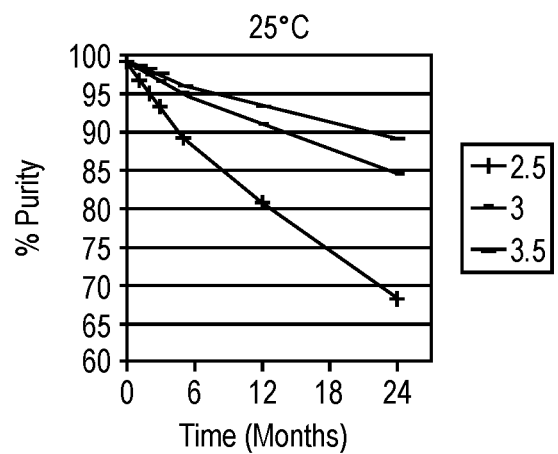
Figure 13C:
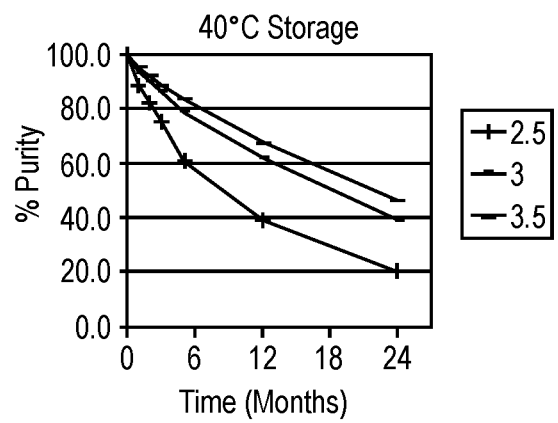

The time course of AMG 416 liquid formulation purity at each pH level is shown in FIG. 13. At all temperatures, the greatest purity was observed at pH 3.5 while the most degradation was observed at pH 2.5. Furthermore, at all temperatures, the purity at pH 3.0 and 3.5 was significantly greater than the purity at pH 2.5. Thus, for example, for the refrigerated samples, the purity at 24 months was 98.3 and 97.7 for the solutions at pH 3.5 and 3.0, respectively, but only 94.8 for the solution at pH 2.5. In addition, the decrease in purity was seen to be related to temperature at all pH levels, with the least degradation observed in the samples incubated at 2-8° C. and the most degradation observed in the samples incubated at 40° C. The major degradant observed at pH 2.5 was the deamidated product and at pH 3.5 the homodimer was observed.

These data confirm that the described formulations are able to maintain adequate stability of AMG 416 over at least a two year shelf-life under refrigerated conditions. The observed degradation is linear in all cases and supports the conclusions based on data extrapolation from earlier experiments. From this data, the optimal pH lies between 3.0 and 3.5 based on the balance between different degradation pathways.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition, comprising:
   etelcalcetide in a liquid formulation comprising water, wherein the formulation has a pH of 2.0 to 5.0 and wherein etelcalcetide is present at a concentration of between about 0.5 mg/mL to about 15 mg/mL.

2. The composition of claim 1, wherein etelcalcetide is present at a concentration of between about 0.5 mg/mL to about 10 mg/mL.

3. The composition of claim 2, wherein the formulation has a pH of 2.5 to 4.50.

4. The composition of claim 1, wherein the pH is maintained by a pharmaceutically acceptable buffer.

5. The composition of claim 4, wherein the buffer is succinate.

6. The composition of claim 1, wherein the etelcalcetide is present as etelcalcetide hydrochloride.

7. The composition of claim 1, further comprising a pharmaceutically acceptable tonicity modifier.

8. The composition of claim 7, wherein the tonicity modifier is NaCl.

9. A liquid composition, comprising: between about 0.5 mg/mL to 15 mg/mL of etelcalcetide hydrochloride in aqueous solution, a succinate buffer that maintains at a pH of between about 2.5 to 4.5, and sodium chloride.

10. A method for treating secondary hyperparathyroidism (SHPT), comprising: parenterally administering the composition according to claim 1 to a subject in need thereof.

11. The method of claim 10, wherein parenterally administering is via intravenous injection.

12. The method of claim 10, wherein the composition comprises etelcalcetide hydrochloride.

13. The method of claim 10, wherein the pH is maintained by a pharmaceutically acceptable succinate buffer.

* * * * *